(12) United States Patent
Boudreaux

(10) Patent No.: US 10,335,129 B2
(45) Date of Patent: Jul. 2, 2019

(54) METHODS AND DEVICES FOR AUTO RETURN OF ARTICULATED END EFFECTORS

(71) Applicant: Ethicon Endo-Surgery, LLC, Guaynabo, PR (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 504 days.

(21) Appl. No.: 14/943,451

(22) Filed: Nov. 17, 2015

(65) Prior Publication Data
US 2017/0135712 A1   May 18, 2017

(51) Int. Cl.
*A61B 17/00*     (2006.01)
*A61B 18/14*     (2006.01)
(Continued)

(52) U.S. Cl.
CPC .... *A61B 17/00234* (2013.01); *A61B 18/1445* (2013.01); *A61B 17/07207* (2013.01); *A61B 17/29* (2013.01); *A61B 2017/003* (2013.01); *A61B 2017/00309* (2013.01); *A61B 2017/00323* (2013.01); *A61B 2017/00367* (2013.01); *A61B 2017/00371* (2013.01); *A61B 2017/00393* (2013.01)

(58) Field of Classification Search
CPC ...... A61B 2017/2927; A61B 2017/293; A61B 2017/00393; A61B 2017/003; A61B 2017/00367; A61B 17/00234; A61B 18/1145

USPC .......................................................... 606/114
See application file for complete search history.

(56) References Cited

U.S. PATENT DOCUMENTS

2005/0192592 A1*  9/2005  Butler ................. A61B 17/221
                                                         606/114
2010/0076433 A1*  3/2010  Taylor ............... A61B 18/1445
                                                          606/52

(Continued)

OTHER PUBLICATIONS

U.S. Appl. No. 14/658,944 entitled "Methods and Devices for Actuating Surgical Instruments" filed Mar. 16, 2015.

(Continued)

*Primary Examiner* — David C Eastwood
*Assistant Examiner* — Erich Herbermann
(74) *Attorney, Agent, or Firm* — Mintz Levin Cohn Ferris Glovsky and Popeo, P.C.

(57) ABSTRACT

Various exemplary methods and devices for auto return of articulated end effectors are provided. In general, a surgical device can include an end effector configured to articulate. The device can include an actuator configured to be actuated to move the end effector from an articulated position to an unarticulated position. In at least some embodiments, the actuator can also be configured to be actuated to move the end effector from the unarticulated position to the articulated position. In at least some embodiments, the device can include the actuator and include another actuator configured to rotate the end effector about a longitudinal axis of an elongate shaft having the end effector at a distal end thereof. In at least some embodiments, the device can include the actuator and include another actuator configured to articulate the end effector from the unarticulated position to the articulated position.

20 Claims, 32 Drawing Sheets

(51) Int. Cl.
    *A61B 17/29*        (2006.01)
    *A61B 17/072*       (2006.01)

(56)                References Cited

U.S. PATENT DOCUMENTS

2011/0036890 A1*   2/2011   Ma ................... A61B 17/07207
                                                             227/175.2
2011/0184435 A1*   7/2011   Parihar ............ A61B 17/00234
                                                             606/114
2012/0078247 A1    3/2012   Worrell et al.
2012/0179165 A1*   7/2012   Grover .................. A61B 17/00
                                                             606/114
2015/0209059 A1    7/2015   Trees et al.
2015/0209061 A1    7/2015   Johnson et al.
2015/0209573 A1    7/2015   Hibner et al.

OTHER PUBLICATIONS

U.S. Appl. No. 14/659,037 entitled "Flexible Neck for Surgical Instruments" filed Mar. 16, 2015.

* cited by examiner

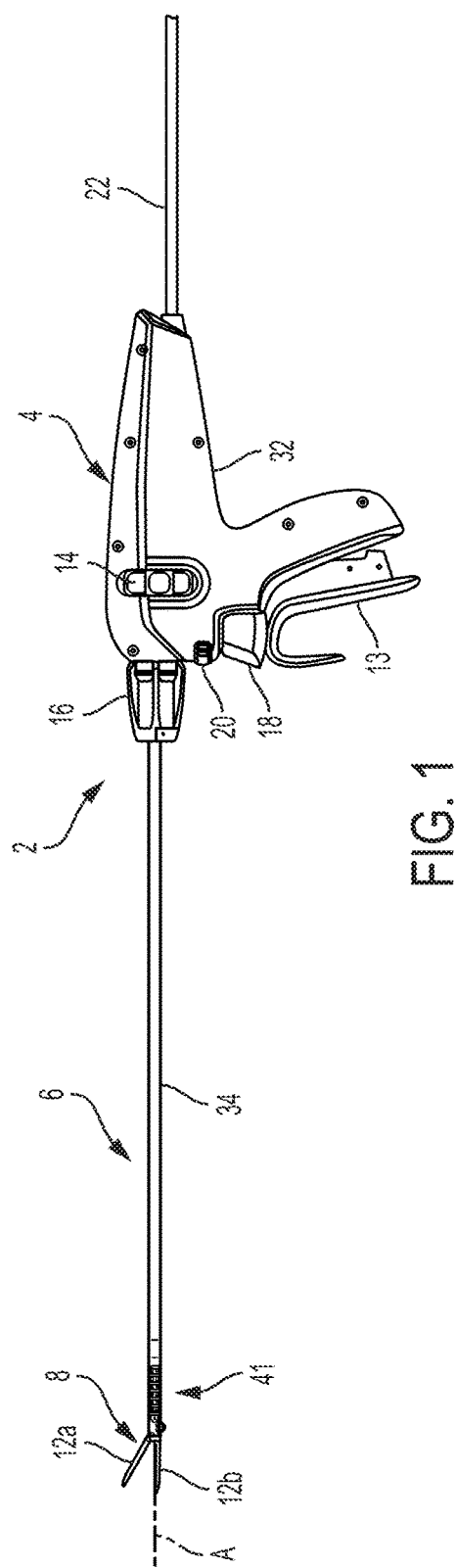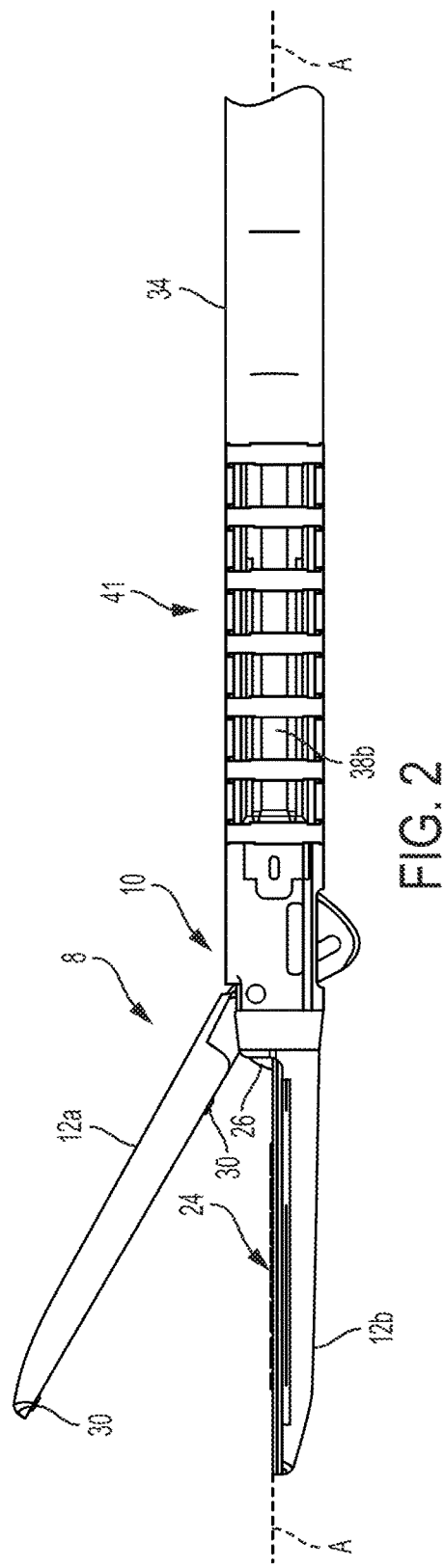
FIG. 1
FIG. 2

METHODS AND DEVICES FOR AUTO RETURN OF ARTICULATED END EFFECTORS

FIELD

Methods and devices are provided for auto return of articulated end effectors.

BACKGROUND

Endoscopic surgical instruments are often preferred over traditional open surgical devices since a smaller incision, or incisions, associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, radiofrequency (RF), laser, etc.).

Some minimally invasive procedures can require that a working end of an endoscopic surgical instrument, which is inserted into the body, be articulated to angularly reorient the working end relative to the tissue. During such a procedure, for example, it is often necessary to reorient the working end such that jaws at the working end are at an angle relative to a shaft of the surgical instrument, while still allowing the jaws to open and close to grasp tissue. However, it can be time consuming to return the working end to its original, non-angled position. Removal of the surgical instrument from the patient with the working end in its original, non-angled position may therefore be delayed. Also, it can be time consuming to move the working end from being articulated in one direction (e.g., left) to an opposite direction (e.g., right). The surgical procedure may thus proceed slower than desired.

Accordingly, there remains a need for methods and devices for return of articulated end effectors.

SUMMARY

In general, methods and devices for auto return of articulated end effectors are provided.

In one aspect, a surgical device is provided that in one embodiment includes a handle having an elongate shaft extending distally therefrom with an end effector at a distal end of the elongate shaft. The end effector has first and second jaws configured to engage tissue therebetween. The surgical device also includes an actuation assembly having first and second movable members and an actuator. The first and second movable members are operatively coupled to the end effector such that axial translation of the first and second movable members causes the end effector to move between a first orientation, in which the end effector is axially aligned with the elongate shaft, and a second orientation, in which the end effector is angularly oriented relative to the elongate shaft. The actuator is engaged with the first and second movable members such that rotation of the actuator is effective to cause axial translation of the first and second movable members. When the end effector is in the second orientation, the first and second movable members can selectively freely axially translate relative to the actuator to cause the end effector to move from the second orientation to the first orientation.

The surgical device can vary in any number of ways. For example, the surgical device can include a second actuator coupled to the handle, and actuation of the second actuator can be configured to disengage the first and second movable members from the actuator and thereby cause the end effector to move from the second orientation to first the orientation. The first and second movable members can each be threadably engaged with the actuator when the end effector is in the second orientation until the actuation of the second actuator, the second actuator can be configured to be actuated with the end effector at any angular orientation relative to the elongate shaft, and/or the actuator can include a rotatable knob and the second actuator can include a switch.

For another example, the first and second movable members can be configured to be disengaged from the actuator with the end effector at any angular orientation relative to the elongate shaft.

For yet another example, the actuation of the actuator can include rotation of the actuator, and the first and second movable members can be configured to automatically axially translate when the actuator is rotated beyond a predetermined threshold amount of rotation. The first and second movable members can each be threadably engaged with the actuator until the actuator is rotated beyond the predetermined threshold amount of rotation.

For still another example, the first and second movable members can be configured to be disengaged from the actuator only once the end effector has reached a maximum amount of angular movement relative to the elongate shaft.

For yet another example, the actuation of the actuator can include rotation of the actuator, and the actuator can be configured to require more force to rotate when the end effector is in the second orientation than when the end effector is in the first orientation.

For still another example, the surgical device can include at least one bias element configured to bias the first and second movable members to a default axial position relative to the actuator, and the first and second movable members can be configured to freely axially translate to the default axial position when the end effector is in the second orientation.

For another example, the first and second members can be configured to become temporarily threadably disengaged from the actuator while the end effector is moving from the second orientation to the first orientation.

For yet another example, the engagement of the first and second movable members with the actuator can include a threaded engagement.

For still another example, the surgical device can include first and second elongate members extending through the elongate shaft. The first movable member can include a first drum coupled to the first elongate member, and the second movable member can include a second drum coupled to the second elongate member. The actuation of the actuator can be configured to simultaneously move the first drum in a first direction and cause axial translation of the first elongate member and move the second drum in a second direction and cause axial translation of the second elongate member. The axial translations of the first and second elongate members can cause the end effector to move from the first orientation to the second orientation. The second direction can be opposite to the first direction.

In another embodiment, a surgical device includes an elongate shaft having a longitudinal axis, an end effector at a distal end of the elongate shaft, and a handle coupled to a proximal end of the elongate shaft and having an actuator disposed thereon. The end effector is movable between a first position aligned along the longitudinal axis and a second position angularly oriented relative to the longitudinal axis. The actuator has a first mode in which movement of the end effector between the first and second positions is controlled by rotation of the actuator, and the actuator has a second mode in which the actuator is operatively disengaged from end effector such that the end effector can move from the second position to the first position.

The surgical device can vary in any number of ways. For example, the surgical device can include a second actuator configured to be actuated so as to cause the actuator to move from the first mode to the second mode and thereby move the end effector from the second position to the first position. The actuator can be configured to automatically return to the first mode from the second mode, and/or the actuator can be configured to move from the first mode to the second mode with the end effector at any non-zero angular orientation relative to the elongate shaft.

For another example, actuation of the actuator can include rotation of the actuator, and the actuation mechanism can be configured to automatically move from the first mode to the second mode when the actuator is rotated beyond a predetermined threshold amount of rotation. The actuator can be configured to automatically return to the first mode from the second mode, and/or actuation of the actuator can include rotation of the actuator and the actuator moving from the first mode to the second mode can be in response to the actuator rotating past a detent.

In another aspect, a method for treating tissue is provided that in one embodiment includes actuating an actuator on a handle of a surgical instrument to move an actuation mechanism threadably engaged with the actuator and thereby cause an end effector at a distal end of an elongate shaft of the surgical instrument to articulate from a substantially zero angle relative to the elongate shaft to a non-zero angle relative to the elongate shaft, the elongate shaft extending distally from the handle, manipulating the surgical instrument to cause the end effector to effect tissue, and disengaging the threaded engagement of the actuation mechanism and the actuator, thereby causing the end effector to move from the non-zero angle to the substantially zero angle.

The method can vary in any number of ways. For example, disengaging the threaded engagement of the actuation mechanism and the actuator can include actuating a second actuator on the handle of the surgical instrument. The first and second actuators can be independently actuatable.

For another example, the actuation of the actuator can include rotation of the actuator, and disengaging the threaded engagement of the actuation mechanism and the actuator can include rotating the actuator beyond a predetermined threshold amount of rotation.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 1 is a side view of one embodiment of a surgical device;

FIG. 2 is a side view of a distal portion of the device of FIG. 1;

DETAILED DESCRIPTION

Figure 3:
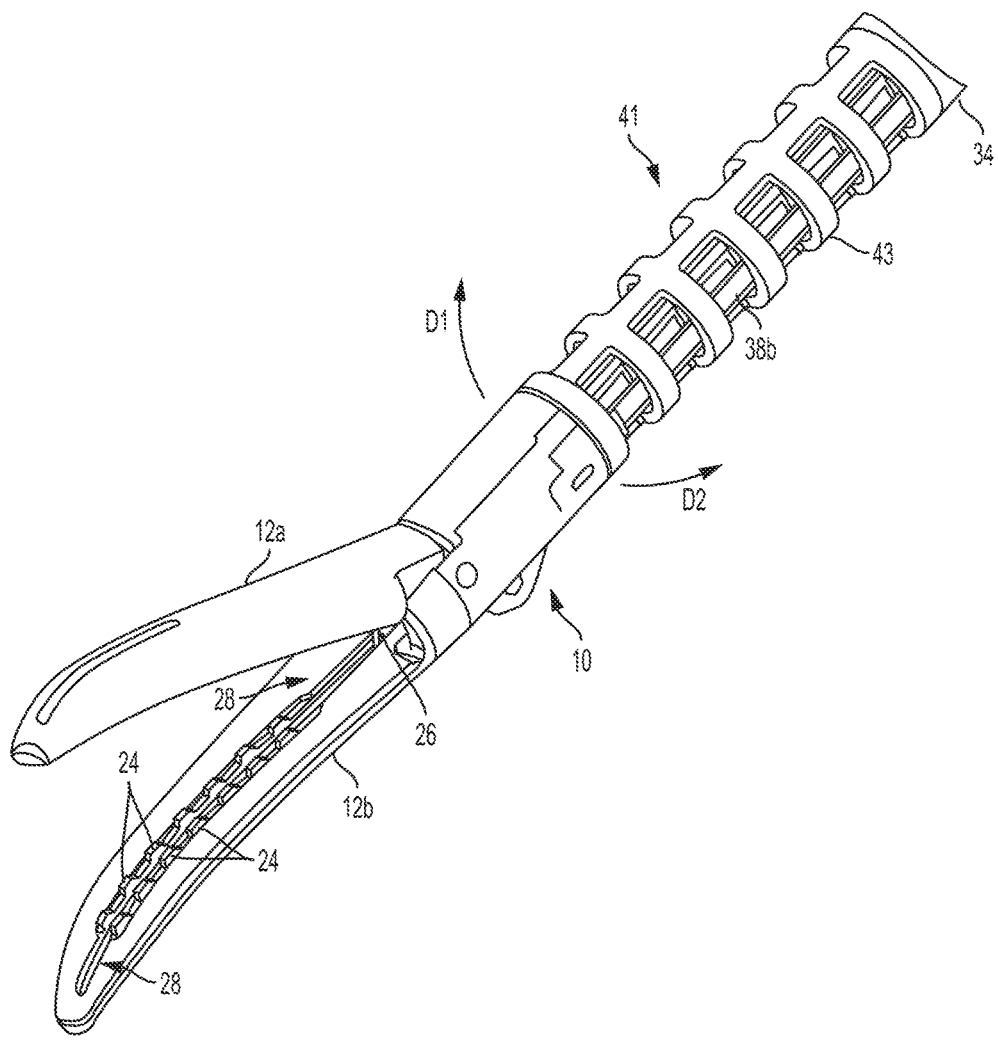
FIG. 3 is a perspective view of a distal portion of the device of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices for auto return of articulated end effectors are provided. In general, a surgical device can include an end effector configured to articulate. The device can include an actuator configured to be actuated to move the end effector from an articulated position to an unarticulated position. The end effector may thus be quickly and predictably returned to its unarticulated position during the performance of a surgical procedure, which may allow for faster repositioning of the end effector to different articulated positions and/or allow the device to be removed more quickly from a patient. As will be appreciated by a person skilled in the art, end effectors of surgical devices are typically in unarticulated positions during removal of the device from a body of the patient at least in minimally invasive surgical procedures.

The actuator configured to be actuated to move the end effector from an articulated position to an unarticulated position can have a variety of configurations. In at least some embodiments, the actuator can also be configured to be actuated to move the end effector from the unarticulated position to the articulated position. The device may thus be simple to use since one control can be used for both angling the end effector toward a longitudinal axis of an elongate shaft having the end effector at a distal end thereof and angling the end effector away from the longitudinal axis of the elongate shaft.

In at least some embodiments, the device can include the actuator configured to be actuated to move the end effector from an articulated position to an unarticulated position and include another actuator configured to rotate the end effector about a longitudinal axis of an elongate shaft having the end effector at a distal end thereof such that the device includes an actuator for end effector auto return and another actuator for rotation. Having two actuators for auto return and rotation may help prevent unintended rotation and help prevent unintended auto return since it can be clear to a user of the device that one actuator is for auto return while another actuator is for rotation. The end effector may thus be less likely to move in an unexpected, potentially dangerous way during use in a body of a patient.

In at least some embodiments, the device can include the actuator configured to be actuated to move the end effector from an articulated position to an unarticulated position and include another actuator configured to articulate the end effector from the unarticulated position to the articulated position. Having two actuators for auto return and articulation may help prevent unintended auto return and help prevent unintended articulation since it can be clear to a user of the device that one actuator is for auto return while another actuator is for angling the end effector from being unarticulated. The end effector may thus be less likely to move in an unexpected, potentially dangerous way during use in a body of a patient. Having two actuators for auto return and articulation may allow the end effector to be moved to the unarticulated position from any articulated position, e.g., at any non-zero angle relative to the elongate shaft, which may speed repositioning of the end effector.

FIG. 1 illustrates one embodiment of a surgical device 2 that can include a proximal handle portion 4 having a shaft assembly 6 extending distally therefrom. The device 2 can generally be configured and used similar to surgical devices having articulatable end effectors described in U.S. patent application Ser. No. 14/658,944 entitled "Methods and Devices for Actuating Surgical Instruments" filed on Mar. 16, 2015, which is hereby incorporated by reference in its entirety.

As shown in FIGS. 1-3, the device 2 can include a working element 8, also referred to herein as an "end effector," coupled to a distal end of the shaft assembly 6. The end effector 8 can be coupled to the shaft assembly 6 at a pivot joint 10. A proximal end of the end effector 8 can be pivotally coupled to the joint 10 at the distal end of the shaft assembly 6.

The end effector 8 can have a variety of sizes, shapes, and configurations. As shown in FIGS. 1-3, the end effector 8, including the first and second jaws 12a, 12b, can be disposed at a distal end of the surgical device 2. The end effector 8 in this illustrated embodiment includes a tissue grasper having a pair of opposed jaws 12a, 12b configured to move between open and closed positions. The end effector 8 can have other configurations, e.g., scissors, a babcock, a retractor, etc. In an exemplary embodiment, the end effector 8 can be rigid. The end effector 8 can include the first, top, or upper jaw 12a and the second, bottom, or lower jaw 12b pivotally connected together at the pivot joint 10.

One or both of the first jaw 12a and the second jaw 12b can include spacers 30 on facing tissue engagement surfaces thereof. The spacers 30 can be configured to maintain a minimum gap of space between the jaws 12a, 12b, e.g., between the tissue engagement surfaces thereof, when the jaws 12a, 12b are in the closed position. The gap of space can help prevent electrodes 24, discussed further below, from becoming damaged and/or from creating a closed circuit loop between the jaws 12a, 12b, as opposed to a closed circuit loop with tissue engaged between the jaws 12a, 12b. In this illustrated embodiment, only the top jaw includes spacers 30 extending therefrom toward the bottom jaw 12b, as shown in FIG. 2. In other embodiments, only the bottom jaw may include spacers, or both the top and bottom jaws may include spacers.

One or both of the jaws 12a, 12b can include the electrodes 24, which can be configured to contact tissue positioned between the jaws 12a, 12b and to apply energy thereto. The electrodes 24 are arranged longitudinally along the bottom jaw 12b in this illustrated embodiment, but the electrodes 24 can be arranged in any of a variety of ways on the upper jaw 12a and/or the lower jaw 12b.

The handle portion 4 can have a variety of sizes, shapes, and configurations. The handle portion 4 can include a main housing 32, which can house a variety of elements therein and can have some elements accessible outside thereof, such as a first actuator 13, a second actuator 14, a third actuator 16, a fourth actuator 18, and a fifth actuator 20.

The first actuator 13 can be configured to effect the opening and closing of the opposed jaws 12a, 12b, e.g., movement of the jaws 12a, 12b toward and away from one another. The jaws 12a, 12b in FIGS. 1-5 are shown in the open position. As in this illustrated embodiment, the upper jaw 12a can be configured to move relative to the bottom jaw 12b, which can remain stationary relative to the shaft assembly 6, to effect the opening and closing of the end effector 8. In other embodiments, in order to effect opening and closing of the end effector, the bottom jaw can be configured to move relative to the upper jaw, or both the upper and lower jaws can be configured to move relative to the shaft assembly.

In an exemplary embodiment, the first actuator 13 can include a gripper arm, also referred to herein as a "closure trigger" and a "movable handle." The closure trigger 13 can, in other embodiments, have different sizes, shapes, and configurations, e.g., no thumb rests, multiple finger loops, different arcuate shape, etc. As shown in FIG. 1, the closure trigger 13 can be pivotally attached to the main housing 32. The closure trigger 13 can be configured to move toward and away from the main housing 32, thereby causing opening and closing of the end effector 8, as discussed further below.

The second actuator 14 can be configured to effect articulation of the end effector 8, e.g., movement of both jaws 12a, 12b in a same direction relative to a longitudinal axis A of the shaft assembly 6. The articulation can be independent of the opening and closing of the jaws 12a, 12b. The end effector 8 in FIGS. 1-5 is shown in an unarticulated position, e.g., at a substantially zero angle relative to the longitudinal axis A. A person skilled in the art will appreciate that the end effector 8 may not be at precisely at a zero angle relative to the longitudinal axis A of the shaft assembly 6 but nevertheless be considered to be at a substantially zero angle relative to the longitudinal axis A of the shaft assembly 6 due to any one or more factors, such as manufacturing tolerance and sensitivity of angle measurement devices. The second actuator 14 can be operatively connected to an actuation mechanism, which can be disposed within the main housing 32 and is discussed further below, such that actuation of the second actuator 14, e.g., manual movement thereof by a user, can cause articulation of the end effector 8. In an exemplary embodiment, the second actuator 14 can be configured to be actuated so as to cause the jaws 12a, 12b to articulate in opposite directions D1, D2 (shown in FIG. 3) relative to the longitudinal axis A.

The second actuator 14 can have a variety of sizes, shapes, and configurations. As in this illustrated embodiment, the second actuator 14 can include a rotatable knob. Rotation of the second actuator 14 in one direction (e.g., clockwise) can be configured to cause articulation of the end effector 8 in the first direction D1 (e.g., right) and rotation of the second actuator 14 in the opposite direction (e.g., counterclockwise) can be configured to cause articulation of the end effector 8 in the second direction D2 (e.g., left). The knob 14 can be rigid. The knob 16 can include a moveable ring, as shown in FIG. 1. The knob 14 can include one or more finger depressions on an exterior surface thereof, as in this illustrated embodiment. The finger depressions can facilitate manual movement of the knob 14 using one or more fingers seated in the finger depressions. As in this illustrated embodiment, the finger depressions can extend around an entire circumference of the knob's exterior surface.

The third actuator 16 can be configured to rotate the shaft assembly 6 and the end effector 8 about the longitudinal axis A of the shaft assembly 6. The third actuator 16 includes a rotatable knob in this illustrated embodiment that can be rotated about the longitudinal axis A, but the third actuator 16 can have a variety of other configurations, e.g., a lever, a button, a movable handle, etc. As in this illustrated embodiment, the third actuator 16 can be configured to continuously and repeatedly rotate the shaft assembly 6 and the end effector 8 360° in both clockwise and counterclockwise directions. In other words, the shaft assembly 6 can be configured for unlimited bi-directional rotation. As will be appreciated by a person skilled in the art, the shaft assembly 6 and the end effector 8 can be rotated less than 360° as desired during performance of a surgical procedure (e.g., rotated 20°, rotated 90°, rotated 150°, etc.) and can be rotated more than 360° as desired during performance of a surgical procedure (e.g., rotated 450°, rotated 480°, rotated 720°, etc.).

Figure 4:
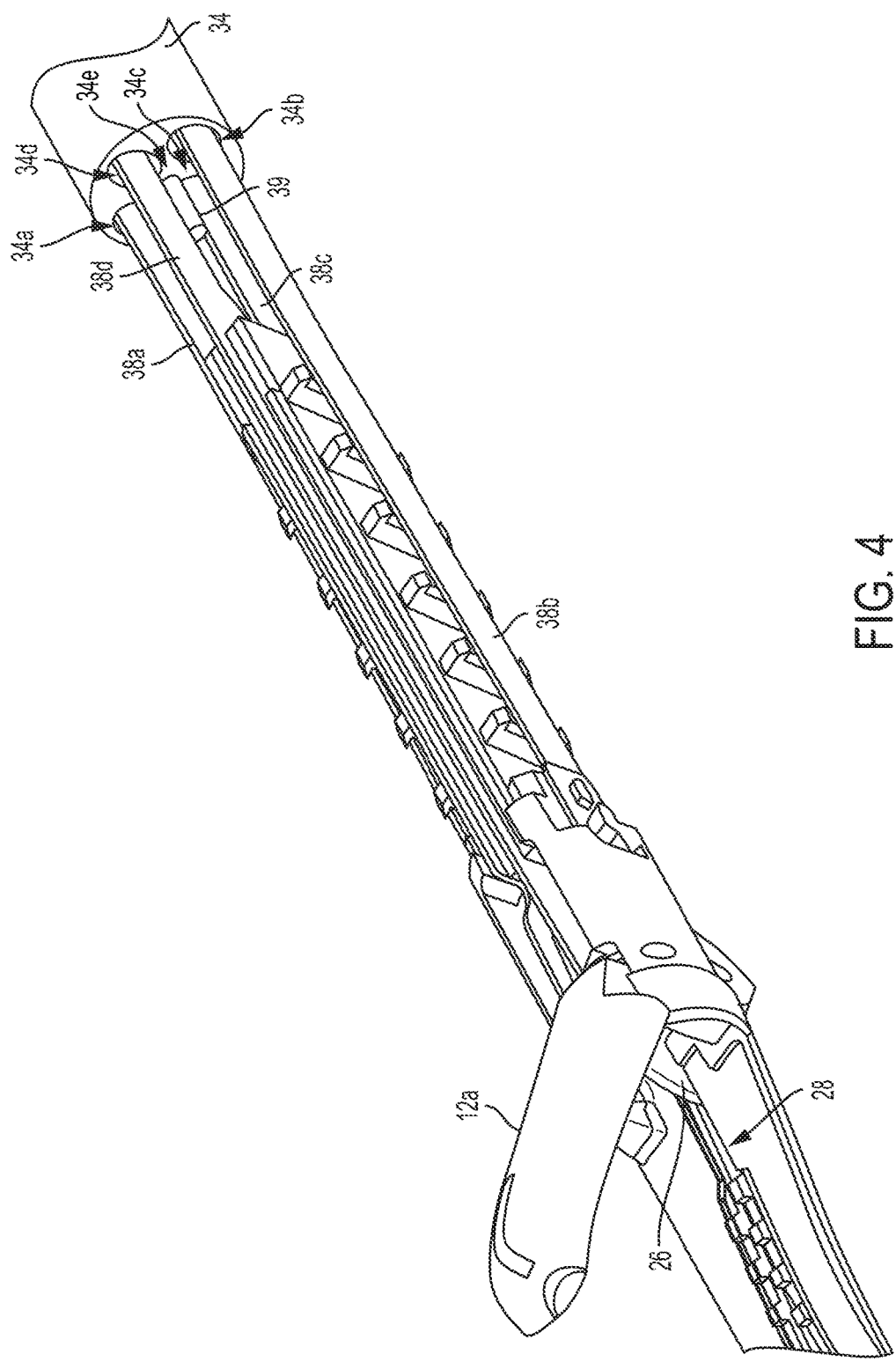
FIG. 4 is a perspective view of a distal portion of the device of FIG. 1 with a flexible outer shell of the device omitted for clarity of illustration.
Figure 5:
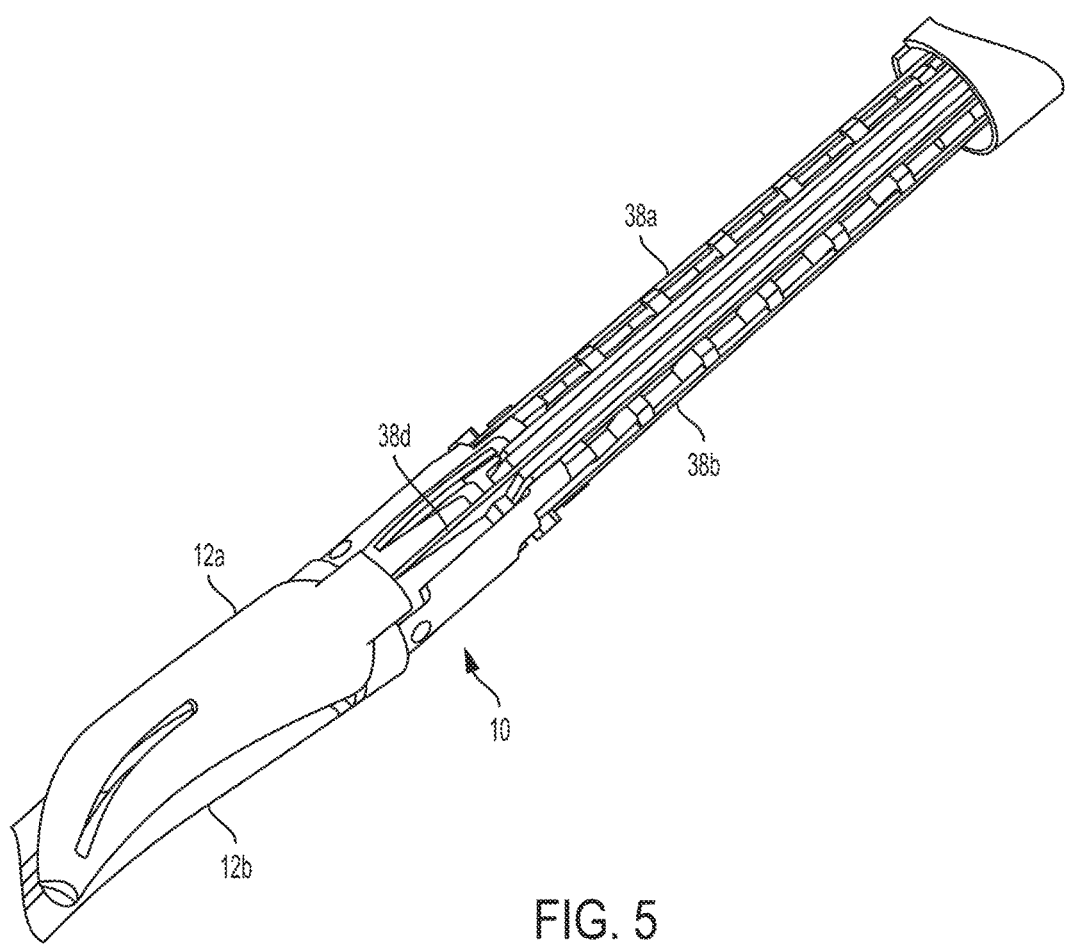
FIG. 5 is another perspective view of the distal portion of the device of FIG. 4.

The fourth actuator 18 can be configured to translate a cutting element 26 (e.g., a knife, a blade, etc.) along the end effector 8. The cutting element 26 can be configured to cut tissue positioned between the jaws 12a, 12b, as will be appreciated by a person skilled in the art. As shown in FIGS. 3 and 4, the jaws 12a, 12b can include an elongate slot 28 therein (the slot in the upper jaw 12a is obscured in FIGS. 3 and 4) through which the cutting element 26 can be configured to slide.

As in this illustrated embodiment, the surgical device 2 can be powered and be configured as an electrosurgical tool configured to apply energy to tissue, such as radiofrequency (RF) energy. The handle portion 4 can have a power cord 22 extending proximally therefrom that can be configured to supply electrical power to the device 2, such as by connecting to a generator, by plugging into an electrical outlet, etc. The fifth actuator 20 can be configured to turn on and off the application of the energy, which can be delivered to tissue via the electrodes 24. The fifth actuator 20 includes a button in this illustrated embodiment, but the fifth actuator 20 can have other configurations, e.g., a knob, a lever, a movable handle, a switch, etc. In other embodiments, the surgical device can be unpowered, e.g., not be configured to apply energy to tissue.

The shaft assembly 6 can have a variety of sizes, shapes, and configurations. The shaft assembly 6 can have any longitudinal length, although in an exemplary embodiment it can be long enough to allow the handle portion 4 to be manipulated outside a patient's body while the shaft assembly 6 extends through an opening in the body with the end effector 8 disposed within a body cavity, e.g., have a longitudinal length of about 33 cm. In this way, the end effector 8 can be easily manipulated when the device 2 is in use during a surgical procedure. The shaft assembly 6 can have any diameter. For example, the shaft assembly's diameter can be less than or equal to about 15 mm, e.g., less than or equal to about 10 mm, less than or equal to about 7 mm, less than or equal to about 5 mm, etc., which can allow for insertion of the shaft assembly 6 through an minimally invasive access device, such as during a laparoscopic surgical procedure. The end effector 8 mated to the shaft assembly's distal end can have a diameter equal to or less than the shaft assembly's diameter, at least when the jaws 12a, 12b are in the closed position, which can facilitate insertion of the device's distal portion into a patient's body.

As in this illustrated embodiment, the shaft assembly 6 can include an outer elongate shaft 34 (also referred to herein an "outer shell") and at least one actuation shaft extending between the handle portion 4 and the end effector 8. The one or more actuation shafts can be configured to facilitate articulation of the end effector 8, to facilitate opening/closing of the end effector 8, and/or to facilitate movement of the cutting element 26 along the end effector 8. As in this illustrated embodiment, the device 2 can include first and second actuation shafts configured to facilitate articulation of the end effector 8, a third actuation shaft configured to facilitate opening/closing of the end effector 8, and a fourth actuation shaft configured to facilitate movement of the cutting element 26 along the end effector 8. In other embodiments, a surgical device can include any combination of the actuation shafts configured to facilitate articulation of the end effector, opening/closing of the end effector, and movement of the cutting element along the end effector, e.g., only include the first and second actuation shafts; only include the fourth actuation shaft; include the first, second, and third actuation shafts; include the third and fourth actuation shafts; etc. The actuation shafts can each have relatively small diameters, which can facilitate their inclusion in a device configured to use in a minimally invasive surgical procedure. In an exemplary embodiment, the actuation shafts can each have a diameter of about 0.04 in. In an exemplary embodiment, the outer shell 34 can have a diameter in a range of about 0.2 in. to 0.221 in. A person skilled in the art will appreciate that an element may not have a diameter of a precisely value but nevertheless be considered to have a diameter of about that value due to, e.g., manufacturing tolerances.

As in this illustrated embodiment, each of the actuation shafts can include a distal elongate member and a proximal elongate member having a distal end attached to a proximal end of the distal elongate member. The distal end of the proximal elongate member can be attached to the proximal end of the distal elongate member in a variety of ways, such as by welding, crimping, gluing, threading, swaging, stamping, trapping, riveting, etc. In an exemplary embodiment, the distal end of the proximal elongate member can be attached to the proximal end of the distal elongate member by welding or crimping, which can be cost effective for manufacturing and/or which can be a relatively simple process during manufacturing. The proximal elongate member can be a rigid member (e.g., generally unable to flex or bend without cracking, breaking, or otherwise becoming damaged), and the distal elongate member can be a flexible member (e.g., generally able to flex or bend without cracking, breaking, or otherwise becoming damaged). The actuation shaft can be made from one or more materials such as titanium, stainless steel, a stranded cable, etc. The rigid and flexible members of the actuation shaft can be made from the same material or can be made from different materials. In an exemplary embodiment, the actuation shaft can have a yield strength in a range of about 40 to 200 ksi. The rigid nature of the proximal elongate member can facilitate stability of the device 2, which can help ease insertion of the device 2 into a patient's body directly or through an access device such as a trocar. This property of the proximal elongate member can facilitate smooth, stable longitudinal translation of the actuation shaft relative to the outer shaft 34, discussed further below. The rigid nature of the proximal elongate member can facilitate making actuation shafts in a variety of longitudinal lengths for different surgical devices since the proximal elongate member can be cut to a desired longitudinal length, as discussed further below. The flexible nature of the distal elongate member can accommodate articulation of the end effector 8 since the distal elongate member can be configured to bend so as to facilitate articulation of the end effector 8 coupled thereto. The actuation shaft having a rigid portion and a flexible portion can ease manufacturing of the device 2 since an entirely flexible actuation shaft need not be formed, such as by stamping, which is traditionally more expensive than methods to form a rigid member, such as molding or casting. The actuation shaft having a rigid portion and a flexible portion can ease manufacturing of surgical devices since distal elongate members can all be formed with a same longitudinal length and proximal elongate members can be formed at selected, different longitudinal lengths, thereby allowing formation of actuation shafts having different longitudinal lengths appropriate for use in different sized devices and/or reducing costs since it is traditionally more expensive to manufacture a flexible member for actuation of a surgical device than to form a rigid member for actuation of a surgical device.

The proximal and distal elongate members can have a variety of configurations. The proximal elongate member can be rigid, as mentioned above, and can include an elongate rod (as in this illustrated embodiment), an elongate band, etc. The distal elongate member can be flexible, as mentioned above, and can include an elongate rod, an elongate band (as in this illustrated embodiment), a cable, a wire, etc. The distal elongate member being a substantially planar band can help conserve real estate at a distal portion of the device 2. A person skilled in the art will appreciate that a band may not be precisely planar but nevertheless be considered to be substantially planar due to, e.g., manufacturing tolerances.

Figure 6:
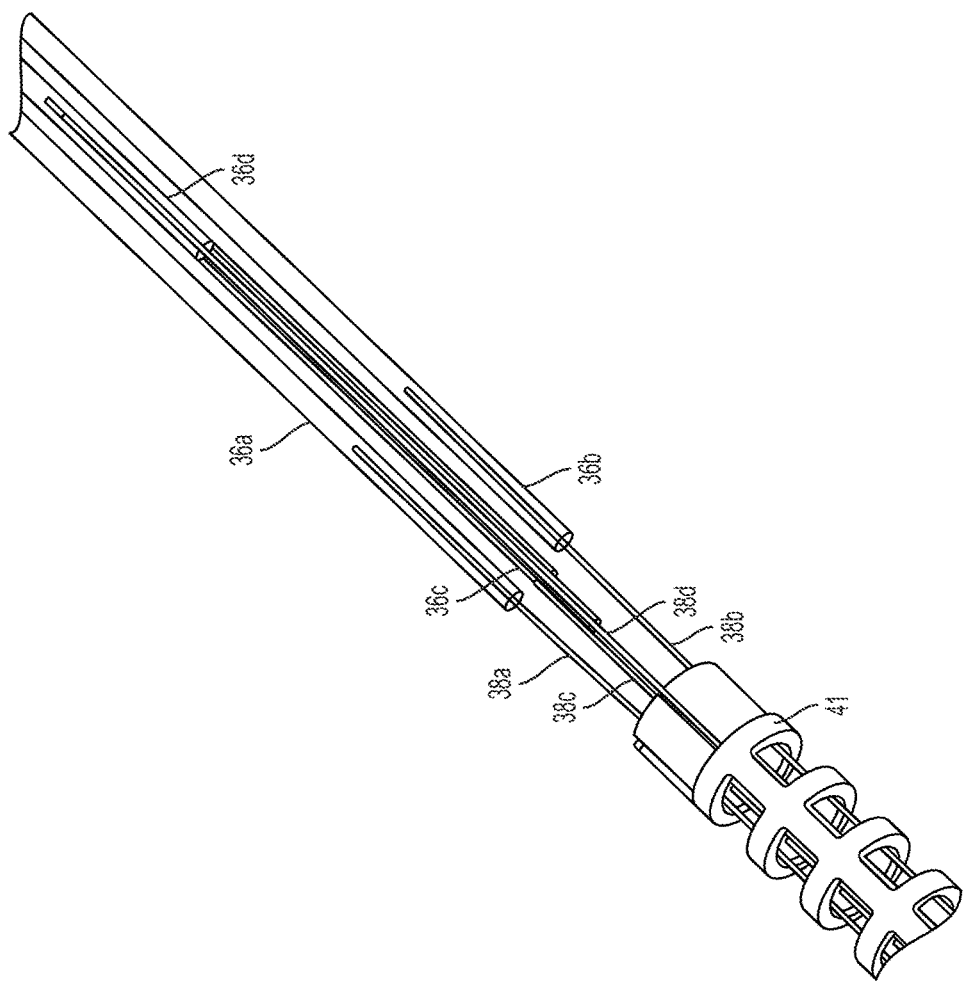
FIG. 6 is a perspective, partial view of a flexible outer shell and actuation shafts of the device of FIG. 1.
Figure 7:
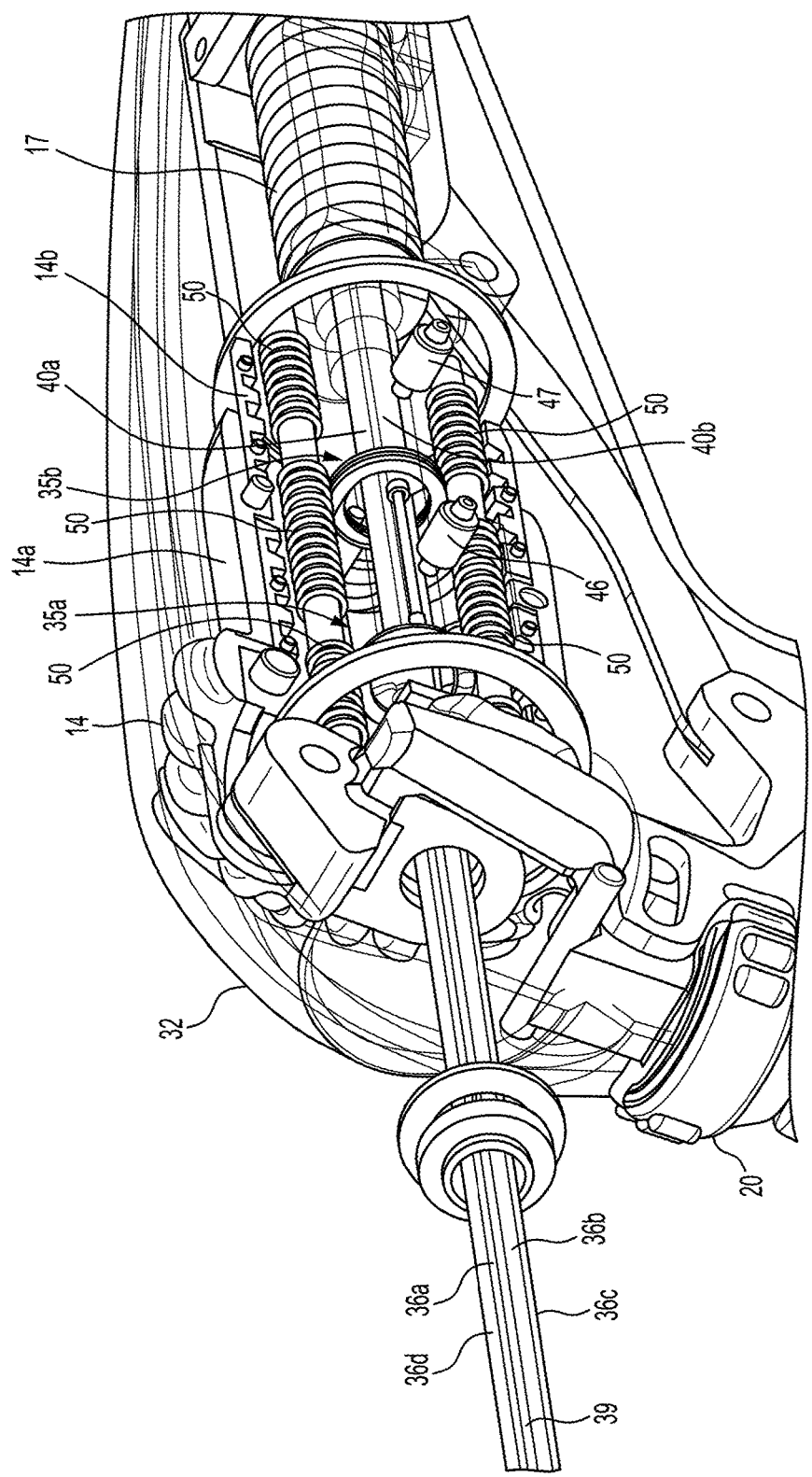
FIG. 7 is a perspective partially cross-sectional view of a proximal portion of the device of FIG. 1 with select elements of the device omitted for clarity of illustration.

As mentioned above, the device 2 in this illustrated embodiment includes four actuation shafts, as shown in FIGS. 6 and 7. The first actuation shaft can be configured to facilitate articulation of the end effector 8 and can include a first proximal elongate member 36a, a first distal elongate member 38a attached to the first proximal elongate member 36a, and a first elongate tube 40a attached to the first proximal elongate member 36a and having an inner lumen in which the first proximal elongate member 36a can be disposed. The second actuation shaft can be configured to facilitate articulation of the end effector 8 and can include a second proximal elongate member 36b, a second distal elongate member 38b attached to the second proximal elongate member 36b, and a second elongate tube 40b attached to the second proximal elongate member 36b and having an inner lumen in which the second proximal elongate member 36b can be disposed. The first and second elongate tubes 40a, 40b can help provide rigidity to the first and second actuation shafts, respectively, in proximal regions thereof, which can help take the positioning load of the respective actuation shafts instead of the first and second proximal elongate members 36a, 36b bearing all the positioning load. The first and second elongate tubes 40a, 40b are enclosed in tubes in this illustrated embodiment, but the first and second elongate tubes can have one or more breaks or openings therein in other embodiments. Proximal elongate members can be attached to their respective tubes in a variety of ways, such as by welding, crimping, gluing, threading, swaging, stamping, trapping, riveting, etc. In an exemplary embodiment, the attachment can be via welding or crimping, which can be cost effective for manufacturing and/or which can be a relatively simple process during manufacturing. In this illustrated embodiment, the proximal elongate members are welded to their respective tubes.

Figure 9:
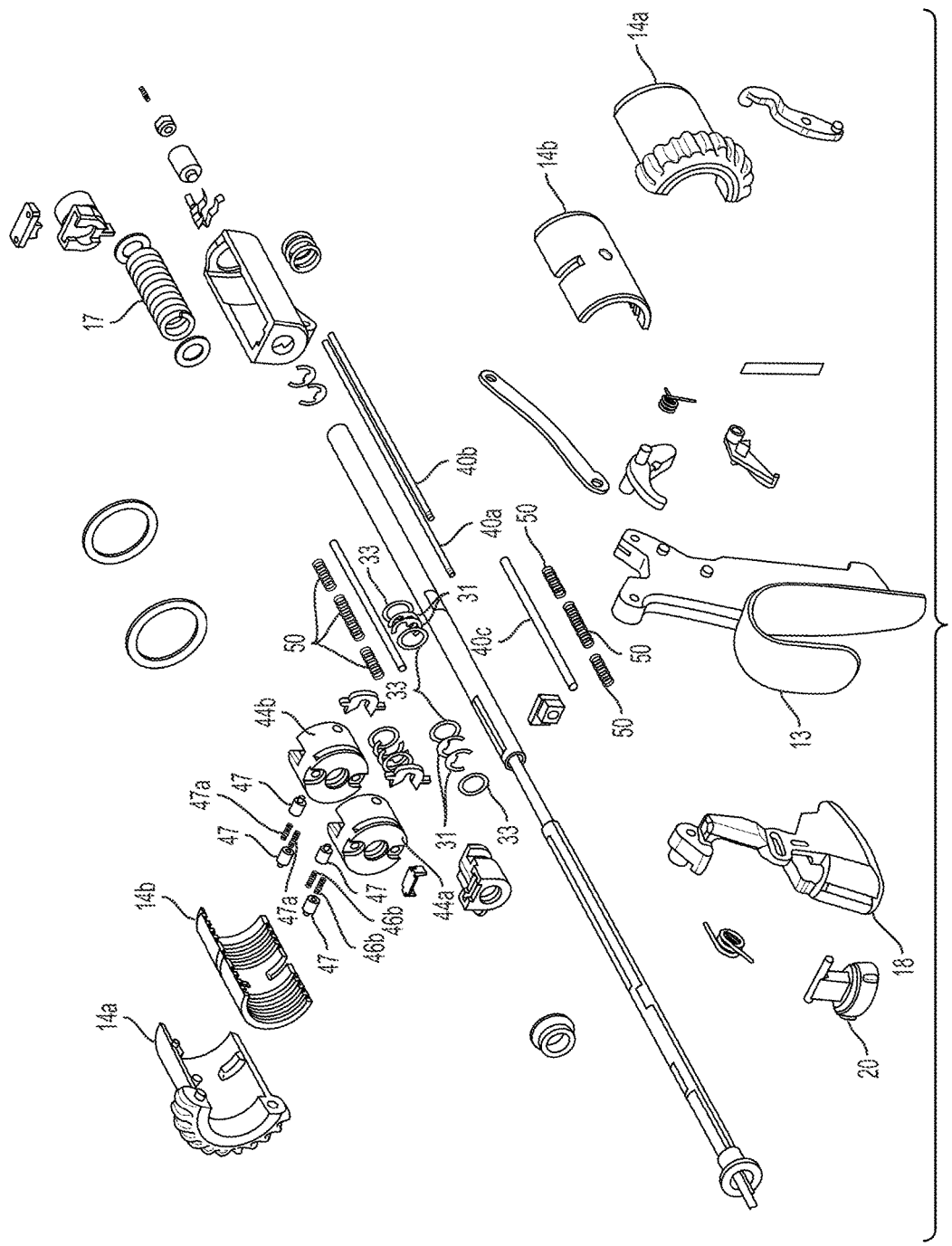
FIG. 9 is an exploded view of a proximal portion of the device of FIG. 1 with select elements of the device omitted for clarity of illustration.

The first and second actuation shafts can be operatively connected to the device's second actuator 14 to facilitate articulation of the end effector 8. The first and second actuation shafts can be operatively connected to the device's second actuator 14 in a variety of ways. As in this illustrated embodiment, as shown in FIGS. 7 and 9, the device 2 can include a first stabilizing member 35a configured to couple the first actuation shaft to the second actuator 14, and can include a second stabilizing member 35b configured to couple the second actuation shaft to the second actuator 14. The first and second stabilizing members 35a, 35b can have a variety of configurations, but in an exemplary embodiment, they are the same as one another. The first stabilizing member 35a and the second stabilizing member 36b can each include a pair of washers 33 and a clip 31 coupled thereto. The pair of washers 33 can be ring-shaped, and the clip 31 (which in this illustrated embodiment includes two clips) can be sandwiched therebetween, as in this illustrated embodiment. As in this illustrated embodiment, the first clip 31 can be configured to clip to the first tube 40a of the first actuation shaft, and the second clip 31 can be configured can be configured to clip to the second tube 40b of the second actuation shaft. As in this illustrated embodiment, the first tube 40a can have a notch (not shown) formed therein configured to receive the first clip 31 therein, and the second tube 40b can have a notch (not shown) formed therein configured to receive the second clip 31 therein.

The third actuation shaft can be configured to facilitate opening and closing of the jaws 12a, 12b and can include a third proximal elongate member 36c, a third distal elongate member 38c attached to the third proximal elongate member 36c, and a third elongate tube 40c (see FIG. 9) having an inner lumen in which the third proximal elongate member 36c can be disposed. The third actuation shaft can be operatively connected to the first actuator 13 in a way such that actuation of the first actuator 13, e.g., movement of the closure trigger 13, can cause opening and closing of the end effector 8. Movement of the closure trigger 13 from an open position shown in FIGS. 1, 7, and 8, in which the end effector 8 is open, to a closed position, in which the end effector 8 is closed, can be achieved by moving the closure trigger 13 toward the main housing 32 can cause the third actuation shaft, and the third actuation shaft's third tube, to move proximally. Likewise, movement of the closure trigger 13 from the closed position to the open position can cause the end effector 8 to open. The third actuation shaft can be operatively connected to the first actuator 13 in a variety of ways, such as by using a stabilizing member similar to the stabilizing members described herein.

Figure 8:
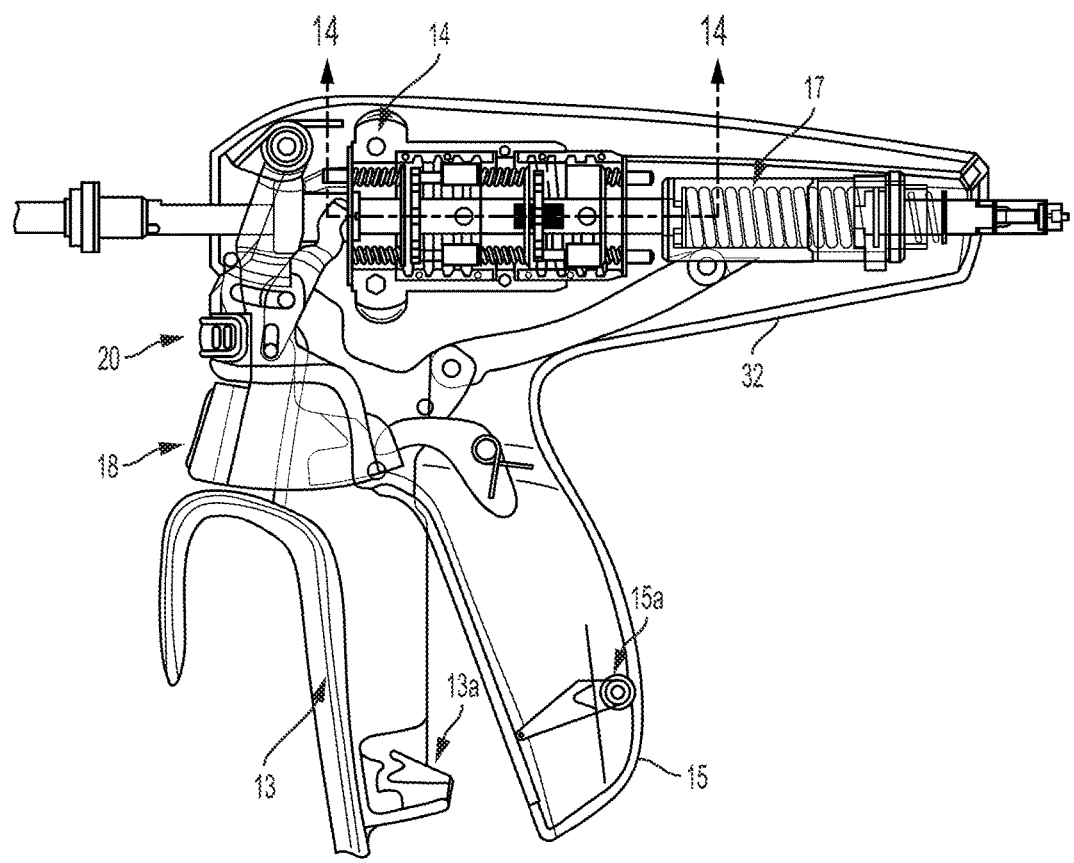
FIG. 8 is a side partially transparent view of a proximal portion of the device of FIG. 1.

As shown in FIG. 8, the device 2 can be configured to lock the closure trigger 13 in the closed position, such as by the closure trigger 13 including a latch 13a configured to engage a corresponding latch 15a on the housing 32, e.g., on a stationary handle 15 thereof, when the closure trigger 13 is drawn close enough thereto so as to lock the closure trigger 13 in position relative to the housing 32, e.g., the stationary handle 15. The closure trigger latch 13a can be configured to be manually released by a user so as to unlock and release the closure trigger 13. A bias spring 17 included in the housing 32 can be coupled to the closure trigger 13 and cause the closure trigger 13 to open, e.g., move away from the stationary handle 15, when the closure trigger 13 is unlocked.

The fourth actuation shaft can be configured to facilitate movement of the cutting element 26 through the end effector 8 and can include a fourth proximal elongate member 36d, a fourth distal elongate member 38d attached to the fourth proximal elongate member 36d, and a fourth elongate tube 40d (see FIG. 9) having an inner lumen in which the fourth proximal elongate member 36d can be disposed. The fourth actuation shaft can be operatively connected to the fourth actuator 18 such that actuation of the fourth actuator 18 can be configured to cause movement of the fourth actuation shaft and thereby move the cutting element 26 along the end effector 8. The fourth actuation shaft can be operatively connected to the fourth actuator 18 in a variety of ways. As in this illustrated embodiment, the device 2 can include another stabilizing member (obscured in the figures) configured to couple the fourth actuation shaft to the fourth actuator 18. This stabilizing member can be configured similar to the stabilizing members described herein, and can include a pair of washers and a clip coupled thereto that can be configured to clip to the fourth tube 40d of the fourth actuation member. The fourth tube 40d can have a notch (not shown) formed therein configured to receive the third clip therein, as in this illustrated embodiment.

The fifth actuator 20 can be operatively connected to a conductive lead 39 (shown in FIG. 7 and in FIG. 4 with a distal portion thereof absent to ease illustration of other parts of the device 2), which in this illustrated embodiment includes an RF cable, configured to be in electrical communication with the power cord 22 and with the electrodes 24. The actuation of the fifth actuator 20, e.g., pushing the button, can be configured to close a circuit and thereby allow power to be provided to the RF cable 39, which can accordingly allow power to be supplied to the electrodes 24.

The outer elongate shaft 34 of the shaft assembly 6 can have a variety of sizes, shapes, and configurations. The outer shell 34 can be configured to stabilize movement of the actuation shafts during actuation of various actuators. As shown in FIG. 4, the outer shell 34 can include a plurality of inner lumens 34a, 34b, 34c, 34d, 34e extending therethrough, as in this illustrated embodiment. The inner lumens 34a, 34b, 34c, 34d, 34e can be isolated from one another, as in this illustrated embodiment, which can help allow elements disposed in each of the inner lumens 34a, 34b, 34c, 34d, 34e to have different loads without affecting others of the elements and/or can help allow elements disposed in each of the inner lumens 34a, 34b, 34c, 34d, 34e to simultaneously move in different directions. In an exemplary embodiment, a number of the inner lumens 34a, 34b, 34c, 34d, 34e can equal a number of actuator shafts, which in this illustrated embodiment is five, such that each of the actuator shafts can be disposed in its own one of the inner lumens 34a, 34b, 34c, 34d, 34e. In other embodiments, the outer shell 34 can include a number of inner lumens less than a number of actuator shafts. The outer shell 34 can be configured to help protect the actuation shafts from an external environment along a longitudinal length of the outer shell 34. The first, second, third, and fourth actuation shafts can be configured to longitudinally translate within their respective ones of the inner lumens 34a, 34b, 34c, 34d, proximally and distally, in response to actuation of their respective ones of the first, second, third, and fourth actuators 13, 14, 16, 18. In an exemplary embodiment, the first and second actuation shafts configured to facilitate articulation can be slidably seated in ones of the inner lumens 34a, 34b on opposite sides (e.g., left and rights sides) of the outer shell 34, which can facilitate articulation of the end effector 8 in opposite directions (e.g., left and right).

The device 2 can include a bend region 41 configured to facilitate articulation of the end effector 8. The bend region can include a flexible outer shell 43, shown in FIG. 3. The flexible outer shell 43 can, as a flexible member, be configured to flex or bend without cracking, breaking, or otherwise becoming damaged, which can facilitate articulation of the end effector 8. The flexible outer shell 43 can have an inner lumen extending therethrough, an upper spine extending longitudinally therealong, a lower spine extending longitudinally therealong, and a plurality of spaced ribs extending between the upper and lower spines on either side (e.g., left and right sides) of the flexible outer shell 43. The first, second, third, and fourth actuation shafts and the RF cable 39 can each extend through the inner lumen of the flexible outer shell 43, as shown in FIG. 3. Exemplary embodiments of flexible outer shells are further described in U.S. Pat. Pub. No. 2012/0078247 entitled "Articulation Joint Features For Articulating Surgical Device" filed on Sep. 19, 2011, and in U.S. application Ser. No. 14/659,037 entitled "Flexible Neck For Surgical Instruments" filed on Mar. 16, 2015, which are hereby incorporated by reference in their entireties.

Figure 10:
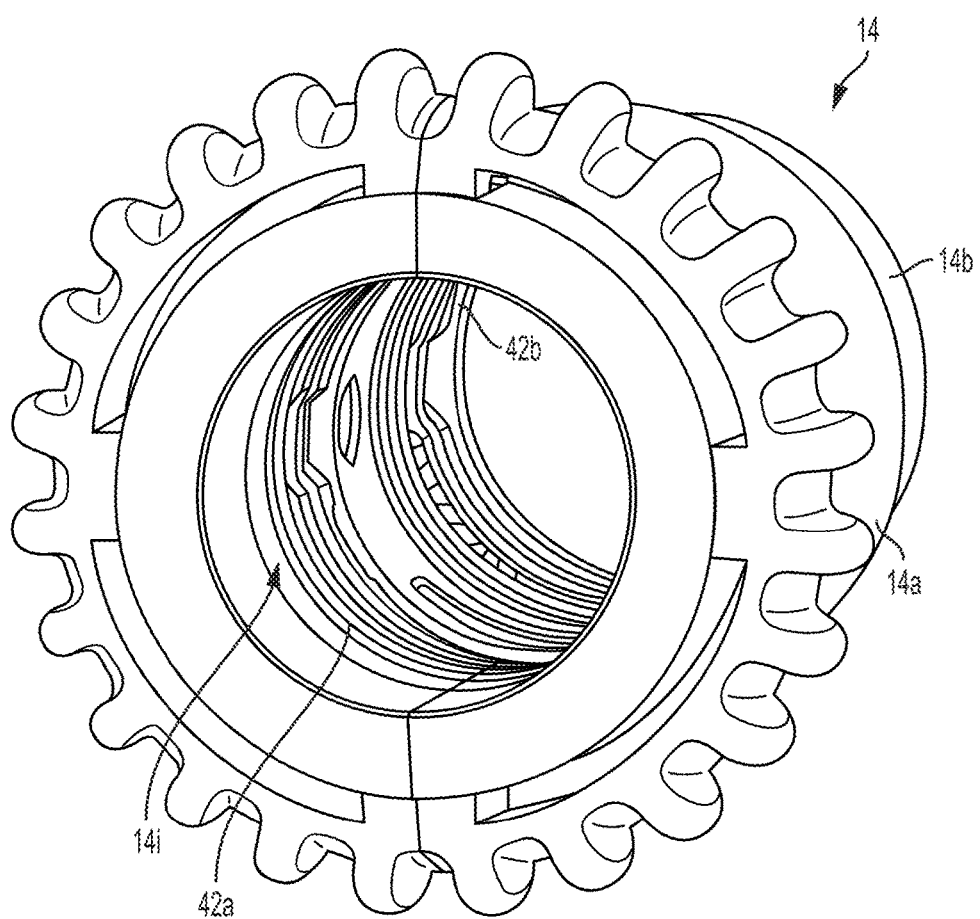
FIG. 10 is a perspective view of an actuator of the device of FIG. 1.
Figure 11:
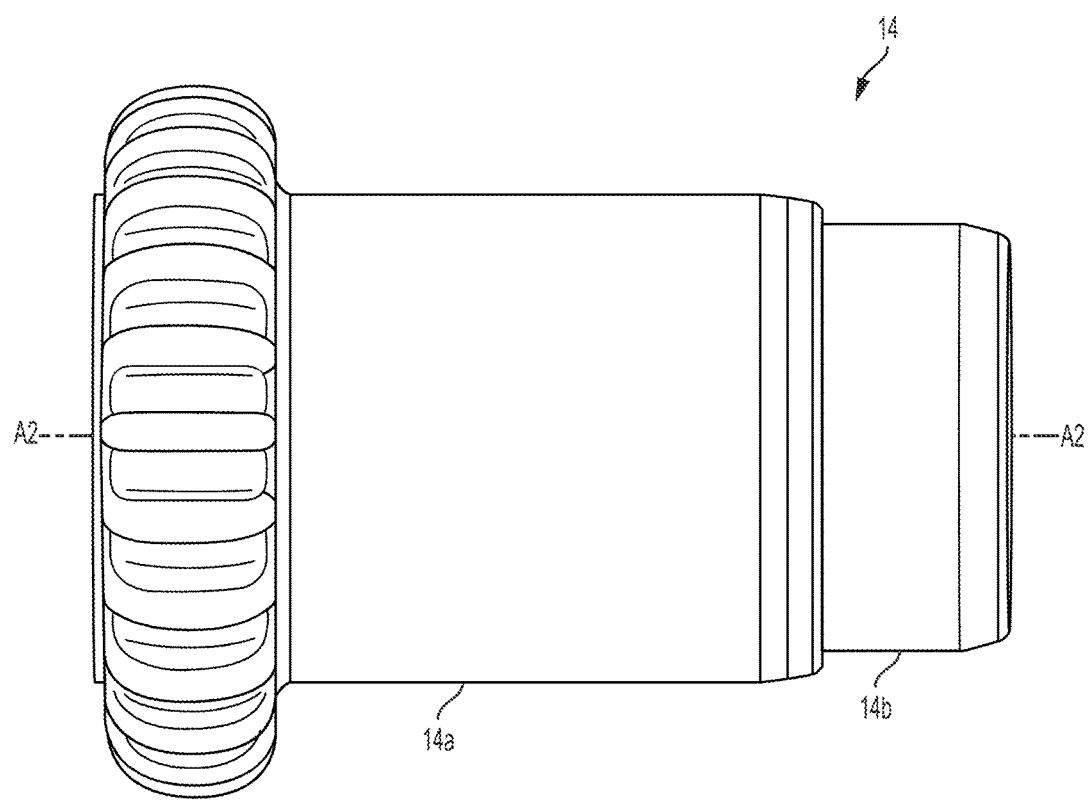
FIG. 11 is a side view of the actuator of FIG. 10.
Figure 12:
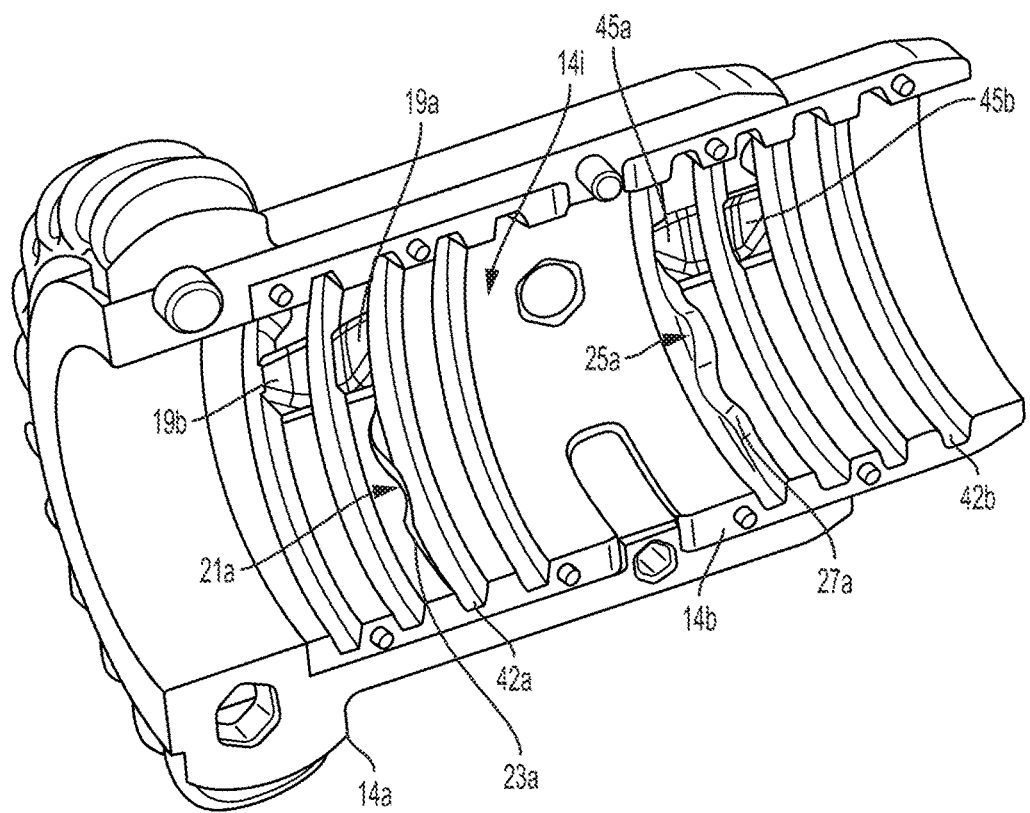
FIG. 12 is a perspective cross-sectional view of the actuator of FIG. 10.
Figure 13:
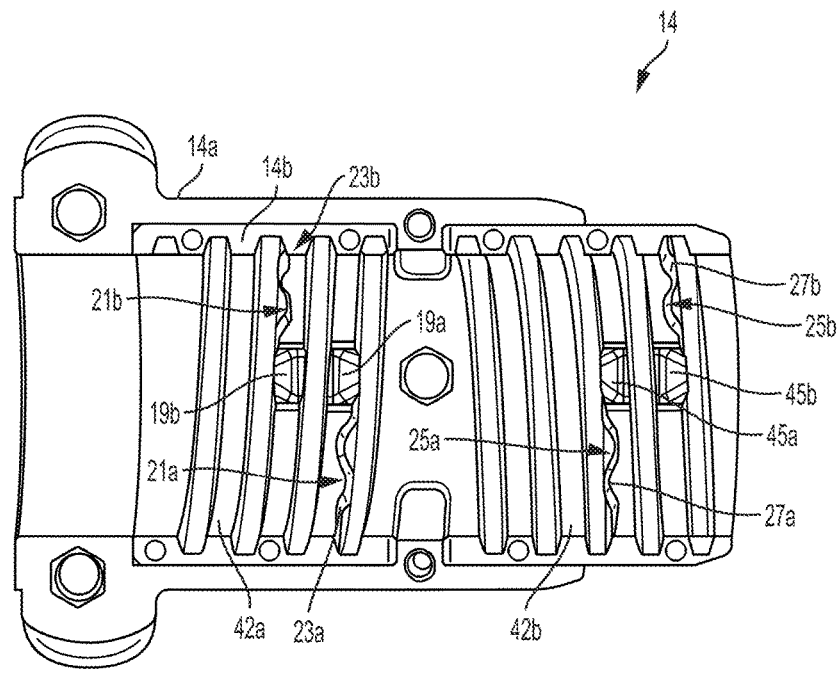
FIG. 13 is a side cross-sectional view of the actuator of FIG. 10.
Figure 14:
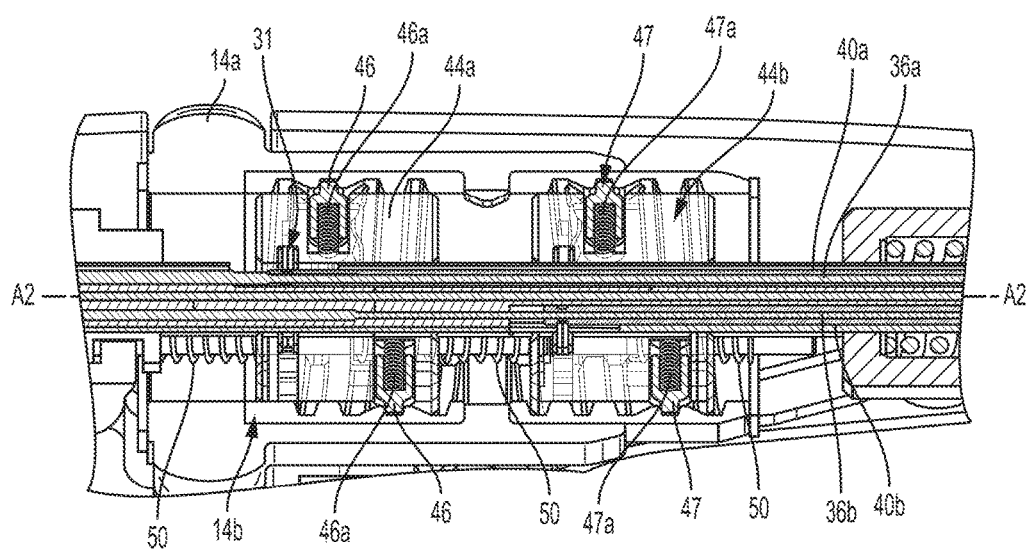
FIG. 14 is a side cross-sectional view of a portion of the device of FIG. 1 within a handle thereof.
Figure 15:
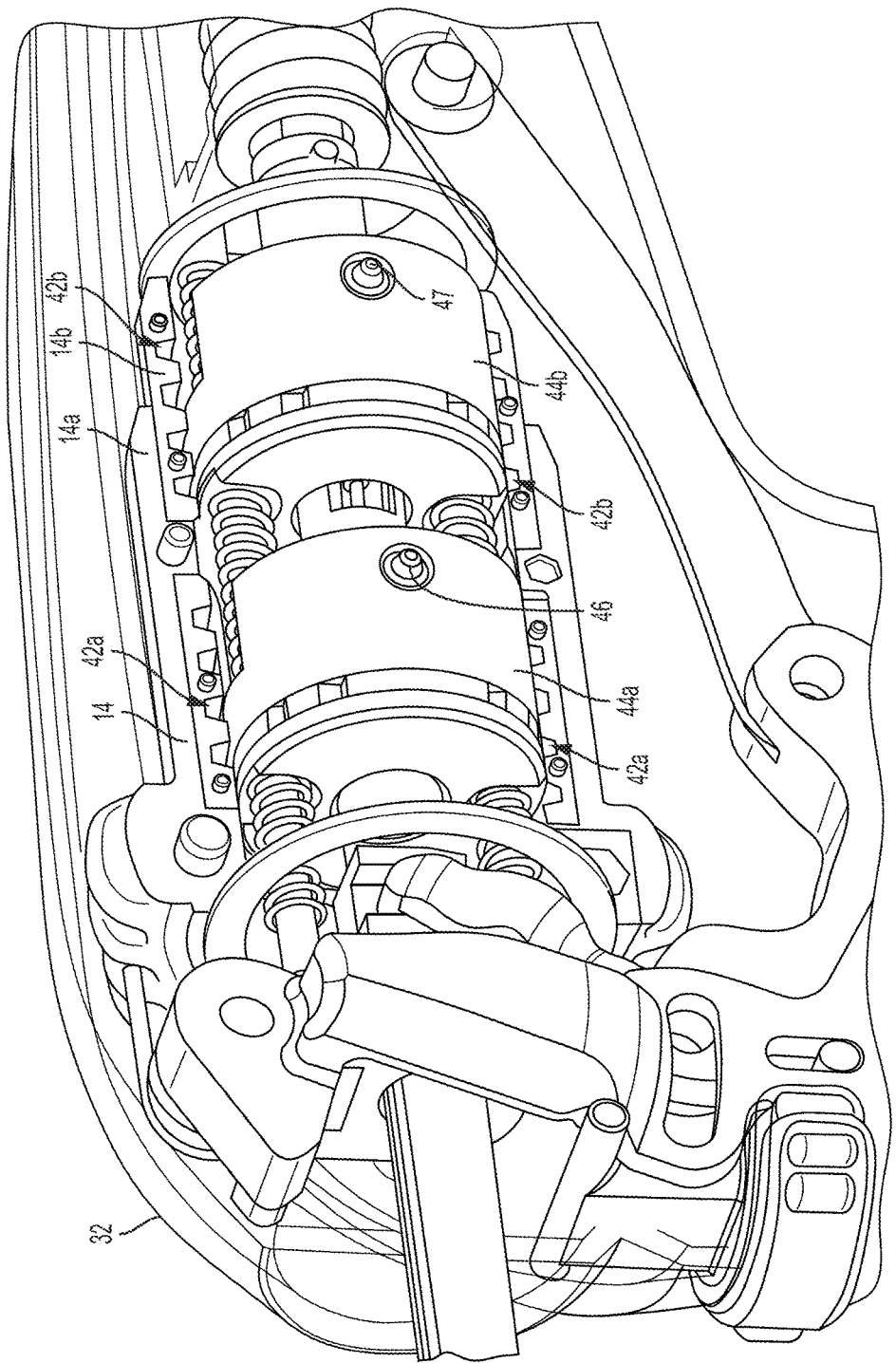
FIG. 15 is a perspective partially cross-sectional view of a proximal portion of the device of FIG. 1 with select elements of the device omitted for clarity of illustration.
Figure 16:
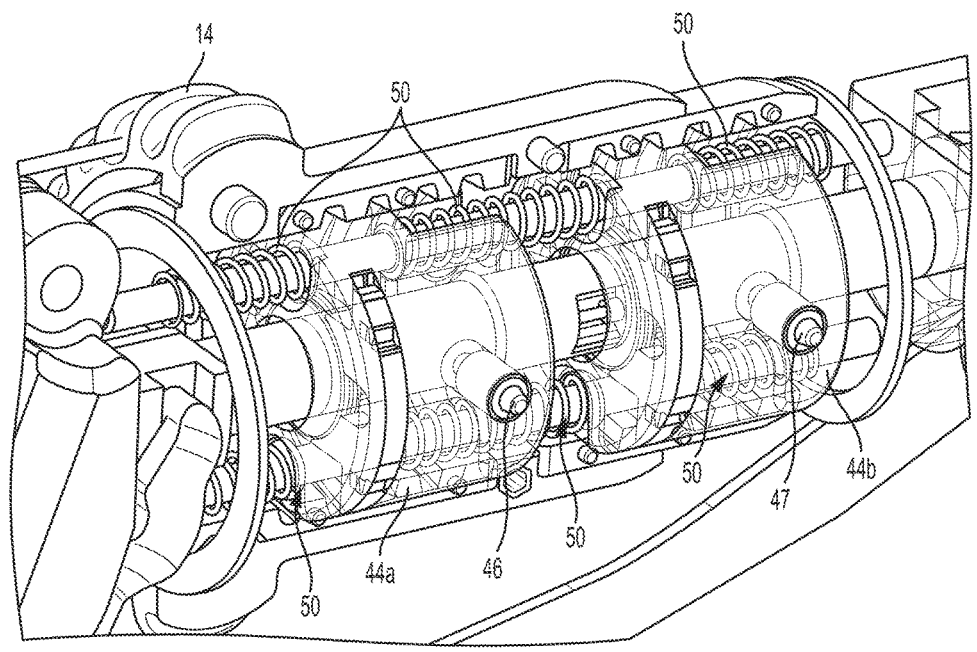
FIG. 16 is a perspective partially transparent, partially cross-sectional view of a portion of the device of FIG. 1 within the handle thereof with select elements of the device omitted for clarity of illustration.
Figure 17:
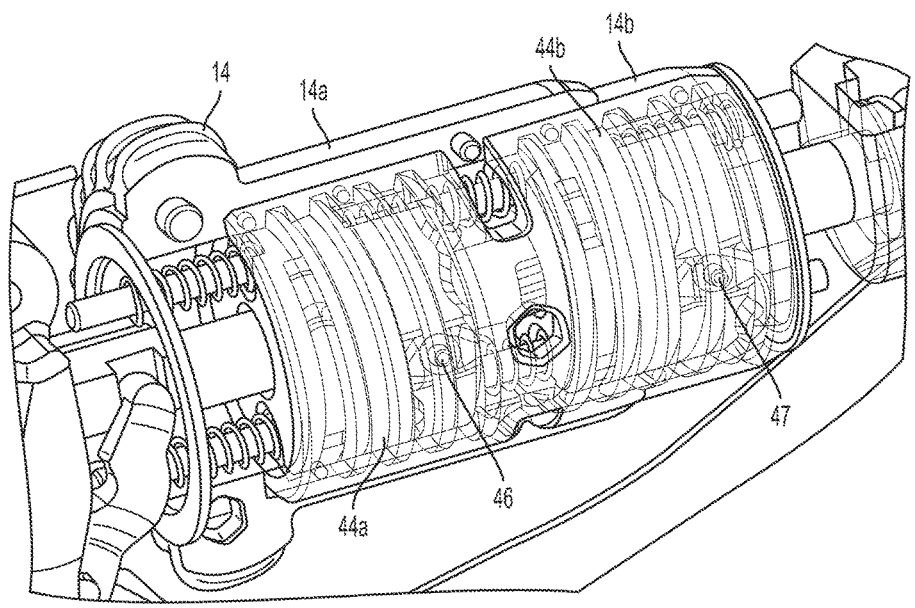
FIG. 17 is a perspective partially transparent, partially cross-sectional view of a portion of the device of FIG. 1 within the handle thereof with select elements of the device omitted for clarity of illustration.

As mentioned above, the second actuator 14 can be configured to facilitate articulation of the end effector 8, which as also mentioned above, can include bending or flexing of the flexible outer shell 43. The actuation mechanism operatively connected to the second actuator 14 can have a variety of sizes, shapes, and configurations. As in this illustrated embodiment, the actuation mechanism can be coupled to the proximal handle portion 4 of the device 2 and can include the second actuator 14, which as described herein can be configured to be manually actuated by a user to effect articulation of the end effector 8. FIGS. 10 and 11 illustrate the second actuator 14 as a standalone element, and FIGS. 12 and 13 show the second actuator 14 in cross-section. As in this illustrated embodiment, the second actuator 14 can include a ring-shaped portion configured to be accessible to a user outside the main housing 32 and can include an elongate tubular portion extending proximally from the ring-shaped portion and being configured to be contained within the main housing 32. The second actuator 14 can thus be cannulated.

The second actuator 14 can include first and second threads 42a, 42b formed in an internal surface 14i thereof. The first thread 42a can be associated with the first actuation shaft, and the second thread 42b can be associated with the second actuation shaft, as discussed further below. The first and second threads 42a, 42b can be independent from one another, as in this illustrated embodiment, with each of the first and second threads 42a, 42b defining separate paths. The first and second threads 42a, 42b can wind in opposite directions around the second actuator 14, e.g., one left-handed and one right-handed. The first and second threads 42a, 42b can have any length around the second actuator's internal surface 14i. In an exemplary embodiment, the first and second threads 42a, 42b can have the same length around the second actuator's internal surface 14i, which may facilitate symmetrical articulation of the end effector 8. The first and second threads 42a, 42b in this illustrated embodiment includes grooves configured to mate with corresponding protrusions configured to slide within the grooves. In other embodiments, the first and second threads 42a, 42b of the second actuator 14 can include protrusions configured to slidably mate with corresponding grooves.

The second actuator 14 can include an obstacle in the pathway of each of the first and second threads 42a, 42b. As discussed further below, the obstacles in the first and second threads 42a, 42b can be configured to facilitate auto return of the end effector 8 from an articulated position, in which the end effector 8 is angled at a non-zero angle relative to the shaft assembly's longitudinal axis A, to an unarticulated position in which the end effector 8 is not articulated, e.g., is at a substantially zero angle relative to the longitudinal axis A so as to be in a substantially linear orientation along the longitudinal axis A.

As in this illustrated embodiment, the obstacle in the pathway of the first thread 42a can include a pair of detents 21a, 21b (also referred to as first and second detents 21a, 21b) and a pair of ramps 23a, 23b (also referred to as first and second ramps 23a, 23b), and the obstacle in the pathway of the second thread 42b can include a pair of detents 25a, 25b (also referred to as third and fourth detents 25a, 25b) and a pair of ramps 27a, 27b (also referred to as third and fourth ramps 27a, 27b). The first detent 21a can configured to cooperate with the first ramp 23a to facilitate auto return of the end effector 8 from an articulated position in one direction (e.g., right), and the second detent 21b can configured to cooperate with the second ramp 23b to facilitate auto return of the end effector 8 from an articulated position in an opposite direction (e.g., left). Similarly, the third detent 25a can configured to cooperate with the third ramp 27a to facilitate auto return of the end effector 8 from an articulated position in one direction (e.g., right), and the fourth detent 25b can configured to cooperate with the fourth ramp 27b to facilitate auto return of the end effector 8 from an articulated position in an opposite direction (e.g., left). The first and third detents 21a, 25a and ramps 23a, 27a can thus be configured to cooperate with one another to facilitate auto return of the end effector 8 from an articulated position in one direction (e.g., right), and the second and fourth detents 21b, 25b and ramps 23b, 27b can thus be configured to cooperate with one another to facilitate auto return of the end effector 8 from an articulated position in an opposite direction (e.g., left).

The second actuator 14 can include a pair of longitudinal cut-outs 19a, 19b in communication with the first thread 42a and a pair of longitudinal cut-outs 45a, 45b in communication with the second thread 42b. As discussed further below, the longitudinal cut-outs 19a, 19b, 45a, 45b can be configured to facilitate auto return of the end effector 8 from its articulated position to its unarticulated position.

As in this illustrated embodiment, the second actuator 14 can include an outer member 14a and an inner member 14b at least partially disposed within the outer member 14a. The outer member 14a can include the ring-shaped portion of the second actuator 14. The inner member 14b can include the first and second threads 42a, 42b and thus can include the obstacles. A proximal portion of the inner member 14b can extend proximally from a proximal end of the outer member 14a, as shown in FIGS. 11-13, and a distal portion of the outer member 14a can be free of the inner member 14b, e.g., a distal end of the inner member 14b can terminate a distance proximal to a distal end of the outer member 14a. The relative positioning of the outer and inner members 14a, 14b may facilitate location of the threads 42a, 42b relative to the device's actuation mechanism disposed within the housing 32 and/or may facilitate location of the ring-shaped portion relative to the housing 32 and thereby facilitate ease of manual manipulation of the second actuator 14 by a hand of a user who is holding the device 2.

The outer and inner members 14a, 14b can be fixedly attached together, as in this illustrated embodiment, such that the outer and inner members 14a, 14b can be configured to move together as a unit when the second actuator 14 is actuated, e.g., when the second actuator 14 is rotated via manipulation of the ring-shaped portion. The outer and inner members 14a, 14b can be fixedly attached together in any of a variety of ways, as will be appreciated by a person skilled in the art, such as by welding, snap fit, adhesive, etc.

In other embodiments, instead of the second actuator including two discrete inner and outer members, the outer and inner members can be an integral unit such that the second actuator is a single piece, e.g., a single molded element.

As mentioned above, the second actuator 14 can be operatively connected to the device's actuation mechanism. The actuation mechanism can include first and second nuts 44a, 44b, also referred to herein as "drums," configured to movably mate with the second actuator 14. The first and second drums 44a, 44b can have a variety of sizes, shapes, and configurations. The first nut 44a can be associated with the first actuation shaft, and the second nut 44b can be associated with the second actuation shaft, as discussed further below. As in this illustrated embodiment, each of the first and second drums 44a, 44b can be generally cylindrical in shape and can be cannulated. The first and second drums 44a, 44b can each be configured to be disposed within the cannulated interior of the second actuator 14, as illustrated in FIGS. 14-17.

The first drum 44a can be biased distally, and the second drum 44b can be biased proximally. The first and second drums 44a, 44b can thus be biased to opposite directions. The device 2 can include one or more biasing elements 50 configured to bias the first drum 44a distally and the second drum 44b distally. The one or more biasing elements 50 in this illustrated embodiment includes a plurality of springs that balance one another to urge the first drum 44a in the distal direction and to urge the second drum 44b in the proximal direction. The bias force provided to the first and second drums 44a, 44b by the one or more biasing elements 50 can be overcome during actuation of the second actuator 14 to move the first and second drums 44a, 44b from their biased distal and proximal positions, as discussed further below. As also discussed further below, the one or more biasing elements 50 can be configured to facilitate auto return of the end effector 8 to its unarticulated position.

The first drum 44a can have one or more pins 46 coupled thereto, and the second drum 44b can have one or more pins 47 coupled thereto. The pin(s) 46 associated with the first drum 44a can be configured to slidably move within the first thread 42a of the second actuator 14, and the pin(s) 47 associated with the second drum 44b can be configured to slidably move within the second thread 42b of the second actuator 14. In other embodiments in which the first and second threads 42a, 42b of the second actuator 14 include protrusions configured to slidably mate with corresponding grooves, the one or more pins of each of the drums 44a, 44b can include grooves configured to engage the protrusions.

Each of the first drum's associated pin(s) 46 can be configured to be alternately seated in and withdrawn from the first thread 42a. The first drum's associated pin(s) 46 can thus be configured to retractable, e.g., move radially inward. Each of the first drum's associated pin(s) 46 can be biased into being seated in the first thread 42a, e.g., biased radially outward. The biasing can be provided by a bias element 46a, which includes a spring in this illustrated embodiment. When a bias force applied to the pin 46 by its associated bias element 46a is overcome, e.g., by interaction of the pin 46 with the first drum's obstacle, the pin 46 can retract from the first thread 42a. Similarly, each of the second drum's associated pin(s) 47 can be configured to be alternately seated in and withdrawn from the second thread 42b. The second drum's associated pin(s) 47 can thus be configured to retractable. Each of the second drum's associated pin(s) 47 can be biased into being seated in the second thread 42b. The biasing can be provided by a bias element 47a, which includes a spring in this illustrated embodiment. When a bias force applied to the pin 47 by its associated bias element 47a is overcome, e.g., by interaction of the pin 47 with the second drum's obstacle, the pin 47 can retract from the second thread 42b. As discussed further below, the retraction of the pin(s) 46 from the first thread 42a and the retraction of the pin(s) 47 from the second thread 42b can cause the end effector 8 to auto return to its unarticulated position from an articulated position.

Each of the drums 44a, 44b is coupled to two pins in this illustrated embodiment. In general, the more pins coupled to a drum, the more stably the drum may move within the second actuator 14, e.g., within the threads 42a, 42b thereof, and/or the more resistance that must be overcome to retract the pins 46, 47 and thus the less likely that the end effector 8 will be accidentally auto-returned to its unarticulated orientation. If the drums 44a, 44b each include a plurality of pins 46, 47, the pins can be equidistantly disposed around a circumference of the drum (180° in this illustrated embodiment in which the drums 44a, 44b each include two pins 46, 47), which may help stabilize movement of the drum within the second actuator 14.

In response to actuation of the second actuator 14, e.g., in response to a user's rotation of the second actuator 12, the second actuator 14 can be configured to rotate about a longitudinal axis A2 (shown in FIGS. 11 and 14) thereof. As in this illustrated embodiment, the second actuator's longitudinal axis A2 can be coaxial with the shaft assembly's longitudinal axis A. The second actuator 14 can be configured to remain stationary along its longitudinal axis A2 during the rotation. In other words, the second actuator 14 can be configured to not move distally or proximally during its rotation. The rotation of the second actuator 14 can cause the first and second drums 44a, 44b disposed within the second actuator 14 and the drums' associated pins 46, 47 threadably engaged with the second actuator (e.g., the first thread 42a threadably engaged with the first drum's pin(s) 46, and the second thread 42b threadably engaged with the second drum's pin(s) 47) to simultaneously move. The opposed threading of the first and second threads 42a, 42b can cause the first and second drums 44a, 44b to move in opposite directions. One of the first and second drums 44a, 44b can move proximally, and the other of the first and second drums 44a, 44b can move distally. The movement of the first and second drums 44a, 44b can include longitudinal translation along the second actuator's longitudinal axis A2, which as in this illustrated embodiment, can also be along the shaft assembly's longitudinal axis A. The first and second drums 44a, 44b can be configured to alternately move distally and proximally during the actuation of the second actuator 14. In other words, rotation of the second actuator 14 in a same direction, whether it be clockwise or counterclockwise, can cause the first drum 44a to first move distally and the second drum 44b to move proximally, and then cause the first and second drums 44a, 44b to switch directions so that the first drum 44a moves proximally and the second drum 44b moves distally. The first actuator shaft can be operatively connected to the first drum 44a, as discussed herein, such that the movement of the first drum 44a can cause a force to be applied to the first actuator shaft and thereby cause corresponding movement of the first actuator shaft, e.g., longitudinal translation of the first drum 44a in a proximal direction can cause longitudinal translation of the first actuator shaft in the proximal direction. The second actuator shaft can be operatively connected to the second drum 44b, as discussed herein, such that the movement of the second drum 44b can cause a force to be applied to the second actuator shaft and thereby cause corresponding movement of the second actuator shaft, e.g., longitudinal translation of the second drum 44b in a distal direction can cause longitudinal translation of the second actuator shaft in the distal direction. The movement of the first and second actuator shafts can be configured to cause the end effector 8 to articulate.

The first actuator shaft can be operatively connected to the first drum 44a and the second actuator shaft can be operatively connected to the second drum 44b in a variety of ways. For example, as mentioned above, the first and second stabilizing members 35a, 35b can be seated within their respective associated drums 44a, 44b.

The first and second stabilizing members 35a, 35b can be configured to facilitate actuation of the second actuator 14, and hence facilitate articulation of the end effector 8, regardless of the rotational position of the shaft assembly 6 about the shaft assembly's longitudinal axis A. In other words, the third actuator 16 can be configured to be at any rotational position about the longitudinal axis A when the second actuator 14 is actuated to articulate the end effector 8. The rotation of the shaft assembly 6 can rotate the first and second actuation shafts of the shaft assembly 6, as discussed herein, which adjusts the position of the first and second actuation shafts relative to the second actuator 14 and to the actuation mechanism. The first and second stabilizing members 35a, 35b can be configured to rotate within and relative to their respective drums 44a, 44b during rotation of the shaft assembly 6 in response to actuation of the third actuator 16. Accordingly, regardless of the rotational position of the first and second stabilizing members 35a, 35b relative to their respective drums 44a, 44b, the first and second actuation shafts coupled to the first and second stabilizing members 35a, 35b can be moved proximally/distally in response to the proximal/distal movement of the drums 44a, 44b during actuation of the second actuator 14. Similar to the first and second stabilizing members 35a, 35b, the third stabilizing member can be configured to facilitate actuation of the fourth actuator 18, and hence facilitate movement of the cutting element 26, regardless of the rotational position of the shaft assembly 6 about the shaft assembly's longitudinal axis A.

Figure 18:
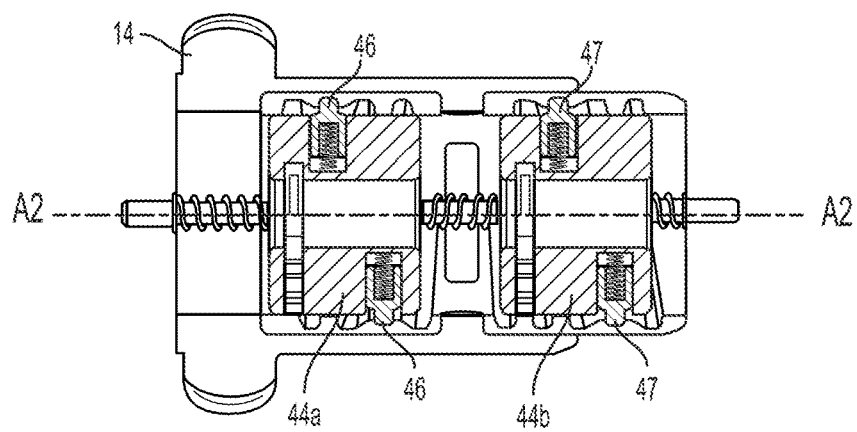
FIG. 18 is a side cross-sectional view of a portion of the device of FIG. 1 within a handle thereof with the actuator of FIG. 10 being in a first position.

FIGS. 18-25 illustrate an embodiment of the actuation of the second actuator 14 and the movement of the first and second drums 44a, 44b, the first pin(s) 46 coupled to the first drum 44a, and the second pin(s) 47 coupled to the second drum 44b in response thereto, thereby causing movement of the first and second actuation shafts and, hence, causing angular movement of the end effector 8. FIG. 18 illustrates a first position of the second actuator 14 in which the first and second drums 44a, 44b are at their outermost positions relative to one another, with the first drum 44a being as far distal as possible for the first drum 44a and the second drum 44b being as far proximal as possible for the second drum 44b. With the second actuator 14 in the first position and the drums 44a, 4b at their farthest from one another, the end effector 8 is at its unarticulated position, e.g., at a substantially zero angle relative to the longitudinal axis A. The first and second actuation shafts have substantially aligned proximal ends, as shown in FIG. 9, when the end effector 8 is unarticulated.

Figure 19:
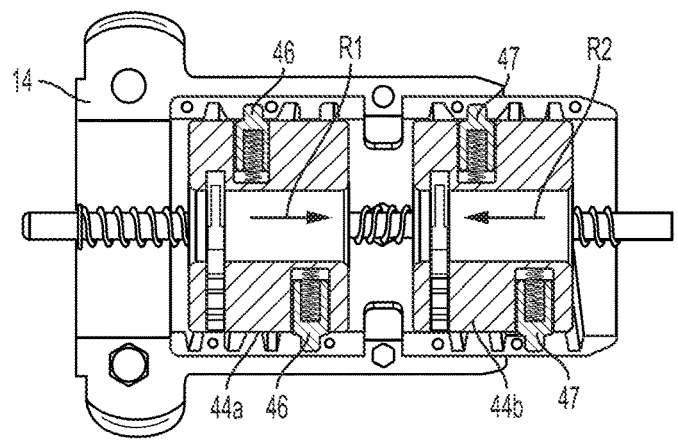
FIG. 19 is a side cross-sectional view of the portion of the device of FIG. 18 with the actuator being in a second position.

FIG. 19 illustrates a second position of the second actuator 14 in which the second actuator 14 has been rotated 90° from the first position of FIG. 18, e.g., rotated clockwise. The rotation of the second actuator 14 has caused the first drum 44a to move proximally, as shown by arrow R1 pointing proximally, and the second drum 44b to move distally, as shown by arrow R2 pointing distally. The first drum 44a has moved within the second actuator 14 due to the threaded engagement of the first drum's first pin(s) 46 with the second actuator's first thread 42a, and the second drum 44b has moved within the second actuator 14 due to the threaded engagement of the second drum's second pin(s) 47 with the second actuator's second thread 42b. The rotation of the second actuator 14 has caused the first and second drums 44a, 44b to move closer together so as to be separated from each other by less distance than in FIG. 18. The proximal movement of the first drum 44a has caused the first actuation shaft operatively connected thereto to correspondingly move proximally. Similarly, the distal movement of the second drum 44b has caused the second actuation shaft operatively connected thereto to correspondingly move distally. The end effector 8 has accordingly articulated to the right, e.g., in the first direction D1 (see FIG. 3), from its position in FIG. 18. The RF cable 39, the third actuation shaft, and the fourth actuation shaft have not moved in response to the actuation of the second actuator 14 between FIGS. 18 and 19.

Figure 20:
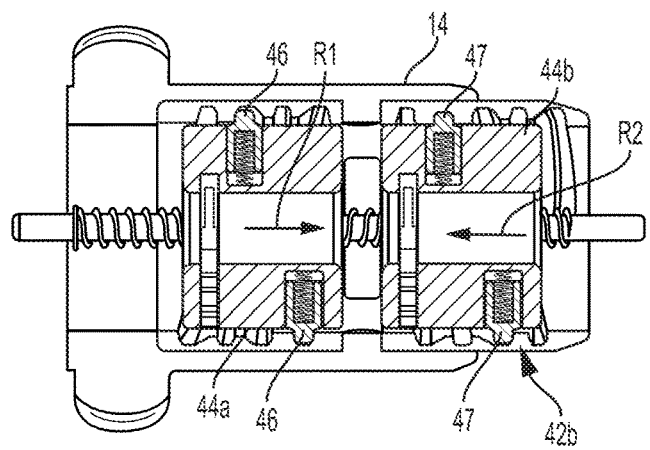
FIG. 20 is a side cross-sectional view of the portion of the device of FIG. 19 with the actuator being in a third position.

FIG. 20 illustrates a third position of the second actuator 14 in which the second actuator 14 has been rotated in the same direction (e.g., clockwise) to be rotated 90° from the second position of FIG. 19 and hence 180° from the first position of FIG. 18. The rotation of the second actuator 14 has caused the first drum 44a to move proximally and the second drum 44b to move distally. The rotation of the second actuator 14 has caused the first and second drums 44a, 44b to move closer together so as to be separated from each other by less distance than in FIG. 19. The proximal movement of the first drum 44a has caused the first actuation shaft operatively connected thereto to correspondingly move proximally. Similarly, the distal movement of the second drum 44b has caused the second actuation shaft operatively connected thereto to correspondingly move distally. The end effector 8 has accordingly articulated further to the right, e.g., in the first direction D1 (see FIG. 3), from its position in FIG. 19. The RF cable 39, the third actuation shaft, and the fourth actuation shaft have not moved in response to the actuation of the second actuator 14 between FIGS. 19 and 20.

Figure 21:
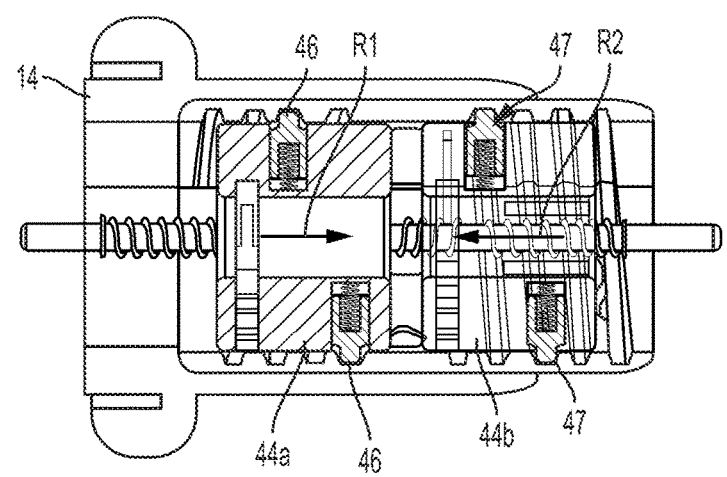
FIG. 21 is a side cross-sectional view of the portion of the device of FIG. 20 with the actuator being in a fourth position.
Figure 22:
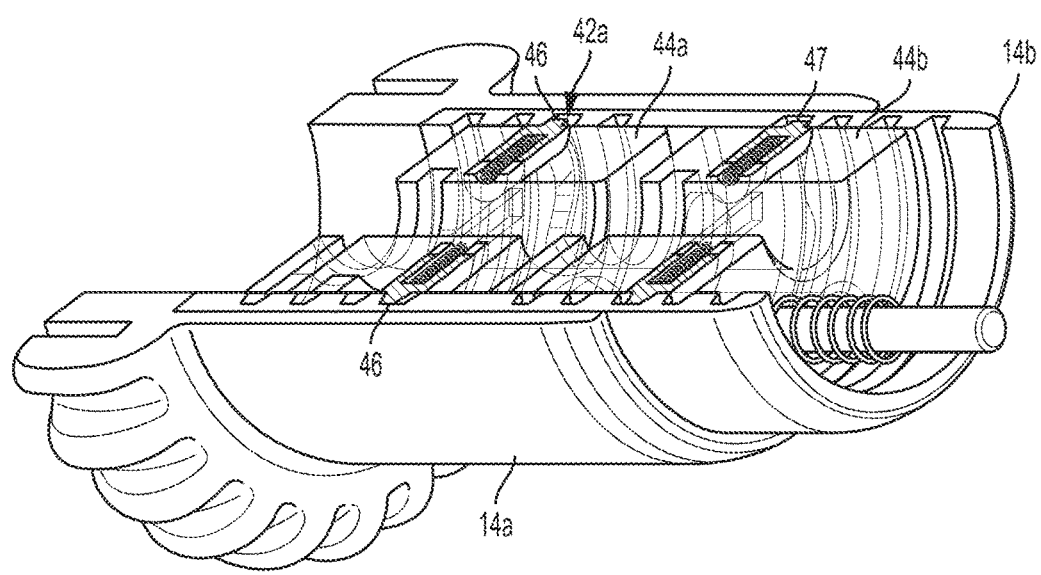
FIG. 22 is a perspective view of the portion of the device of FIG. 21.
Figure 23:
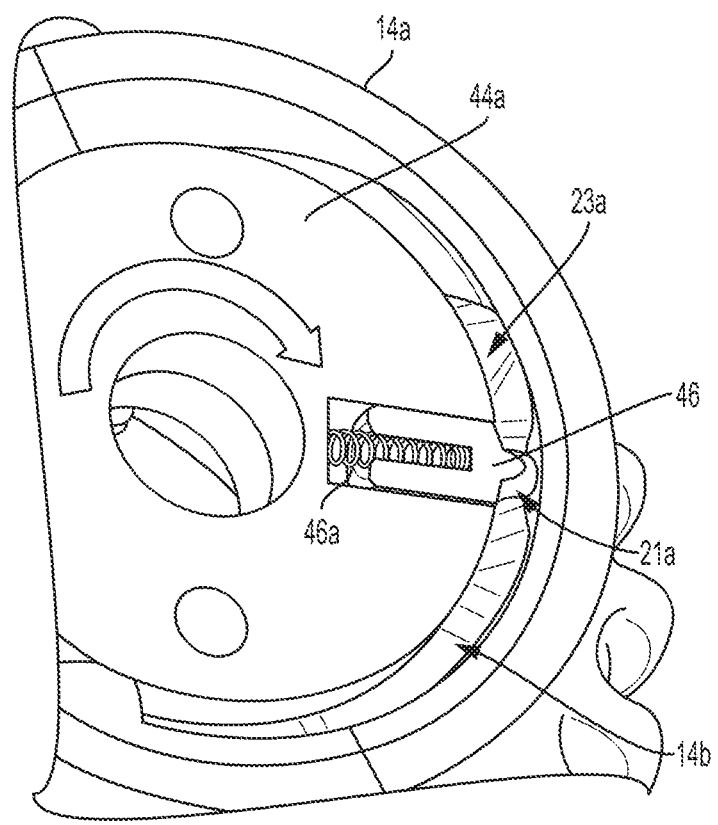
FIG. 23 is a partial perspective view of the portion of the device of FIG. 21.

FIGS. 21-23 illustrate a fourth position of the second actuator 14 in which the second actuator 14 has been rotated in the same direction (e.g., clockwise) 170° from the third position of FIG. 20 and hence 260° from the second position of FIG. 19 and 350° from the first position of FIG. 18. The rotation of the second actuator 14 has caused the first drum 44a to move proximally and the second drum 44b to move distally. The rotation of the second actuator 14 has caused the first and second drums 44a, 44b to move closer together so as to be separated from each other by less distance than in FIG. 20. The first drum's pin(s) 46 have each moved over the ramp 23a and into the detent 21a adjacent thereto and is positioned therein with the second actuator 14 in the fourth position. (If the second actuator 14 had been rotated in the opposite direction, e.g., counterclockwise, the end effector 8 would have instead articulated in the opposite direction, e.g., left, and the first drum's pin(s) 46 would have instead moved over the ramp 23b and into the detent 21b.) The distal movement of the first drum 44a has caused the first actuation shaft operatively connected thereto to correspondingly move distally. Similarly, the second drum's pin(s) 47 have each moved over the ramp 27a and into the detent 25a adjacent thereto and is positioned therein with the second actuator 14 in the fourth position. (If the second actuator 14 had been rotated in the opposite direction, e.g., counterclockwise, the end effector 8 would have instead articulated in the opposite direction, e.g., left, and the second drum's pin(s) 47 would have instead moved over the ramp 27b and into the detent 25b.) The proximal movement of the second drum 44b has caused the second actuation shaft operatively connected thereto to correspondingly move proximally. The end effector 8 has accordingly articulated further to the right, e.g., in the first direction D1 (see FIG. 3), from its position in FIG. 20, and is now at its maximum amount of articulation to the right. The movement of each of the pin(s) 46, 47 over their respective ramps 23a, 25a can be tactilely felt by a user manually manipulating the second actuator 14, since more force will be required to urge the pins 46, 47 over their respective ramps 23a, 25a than to merely slide the pins 46, 47 along their respective threads 42a, 42b, thereby indicating to the user that the end effector 8 has been fully articulated. The RF cable 39, the third actuation shaft, and the fourth actuation shaft have not moved in response to the actuation of the second actuator 14 between FIGS. 20 and 21.

Figure 24:
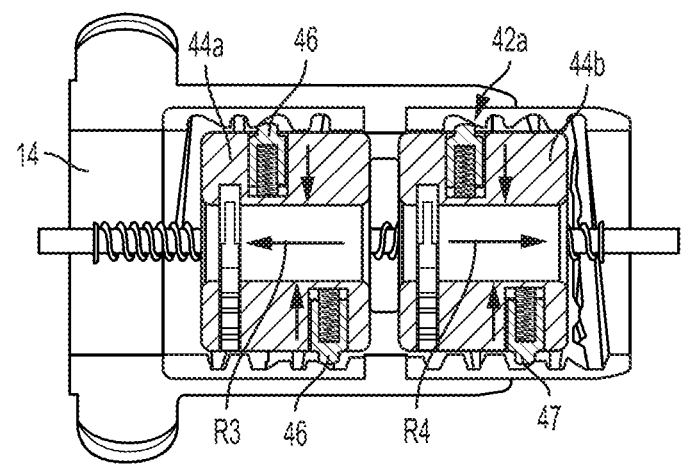
FIG. 24 is a side cross-sectional view of the portion of the device of FIG. 21 with the actuator being in a fifth position.
Figure 25:
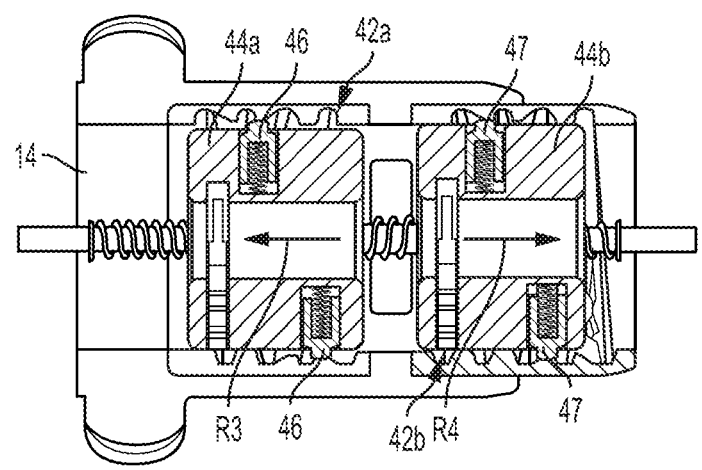
FIG. 25 is another side cross-sectional view of the portion of the device of FIG. 21 with the actuator being in the fifth position.

FIG. 24 illustrates a fifth position of the second actuator 14 in which the second actuator 14 has been rotated in the same direction (e.g., clockwise) 10° from the fourth position of FIG. 21 and hence 180° from the third position of FIG. 20, hence 270° from the second position of FIG. 19, and 360° from the first position of FIG. 18. The rotation of the second actuator 14 has caused the first drum 44a to move distally, as shown by arrow R3, and the second drum 44b to move proximally, as shown by arrow R4. The rotation of the second actuator 14 has caused the first and second drums 44a, 44b to move farther apart so as to be separated from each other by more distance than in FIG. 21. The first drum's pin(s) 46 have moved out of their associated detent 21a and toward the longitudinal cut-out 19a adjacent thereto. The distal direction bias of the first drum 44a due to the one or more biasing elements 50 can force the pin(s) 46 to slide out of the first thread 42a, into the longitudinal cut-out 19a where the pin(s) 46 can slide distally, and back into the first thread 42a. The first drum 44a can thus slide distally within the second actuator 14, as shown in FIG. 25, back to its first position of FIG. 18. Similarly, the second drum's pin(s) 47 have moved out of their associated detent 25a and toward the longitudinal cut-out 45a adjacent thereto. The proximal direction bias of the second drum 44b due to the one or more biasing elements 50 can force the pin(s) 47 to slide out of the second thread 42b, into the longitudinal cut-out 45a where the pin(s) 47 can slide proximally, and back into the second thread 42b. The second drum 44b can thus slide proximally within the second actuator 14 back to its first position of FIG. 18. The first and second drums 44a, 44b can thus each be configured to translate longitudinally within the second actuator 14, with the first drum 44a moving distally and its associated pin(s) 46 sliding distally through the longitudinal cut-out 19a and the second drum 44b moving proximally and its associated pin(s) 47 sliding proximally through the longitudinal cut-out 45a to return to the first position of FIG. 18. The movement of each of the pin(s) 46, 47 out of their respective detents 21a, 25a can be tactilely felt by a user manually manipulating the second actuator 14, since more force will be required to urge the pins 46, 47 out of the detents 21a, 25a than to merely slide the pins 46, 47 along their respective threads 42a, 42b, thereby indicating to the user that the end effector 8 is being returned to its unarticulated position.

The end effector 8 being configured to return to its unarticulated position after the first actuator 14 has been rotated 360° in one direction (either clockwise or counterclockwise) may help prevent over-articulation of the end effector 8, which may break or otherwise damage the end effector 8 and/or other parts of the device 2. Even if a user continues actuating the second actuator 14 (e.g., continues rotating the second actuator 14) has been fully articulated to its maximum extent either in the left direction or the right direction, the end effector 8 will not be urged to continue articulating, which may strain the end effector 8 and/or other device 2 components, which may break or otherwise damage the end effector 8 and/or other strained parts of the device 2. Instead, the end effector 8 will simply return to its unarticulated position. The device 2 can be configured to warn the user that the end effector 8 is about to return to its unarticulated position due to the tactile feel discussed above during actuation of the second actuator 14.

The second actuator 14 can continue rotating in the same direction (e.g., clockwise) after moving back to the first position from the fifth position, continually moving the first drum 44*a* longitudinally proximally and distally and moving the second drum 44*b* alternately to the first drum 44*a*, e.g., distally when the first drum 44*a* is moving proximally. The second actuator 14 can be rotated in an opposite direction (e.g., counterclockwise) at any point, e.g., before, between, or after any of the first, second, third, fourth, and fifth positions, which can allow the end effector's angular position to be angled as desired during the course of performance of a surgical procedure and/or can help accommodate right-handed and left-handed users. The second actuator 14 can stop being rotated at any time so as to hold the end effector 8 in position, whether articulated or unarticulated.

Figure 26:
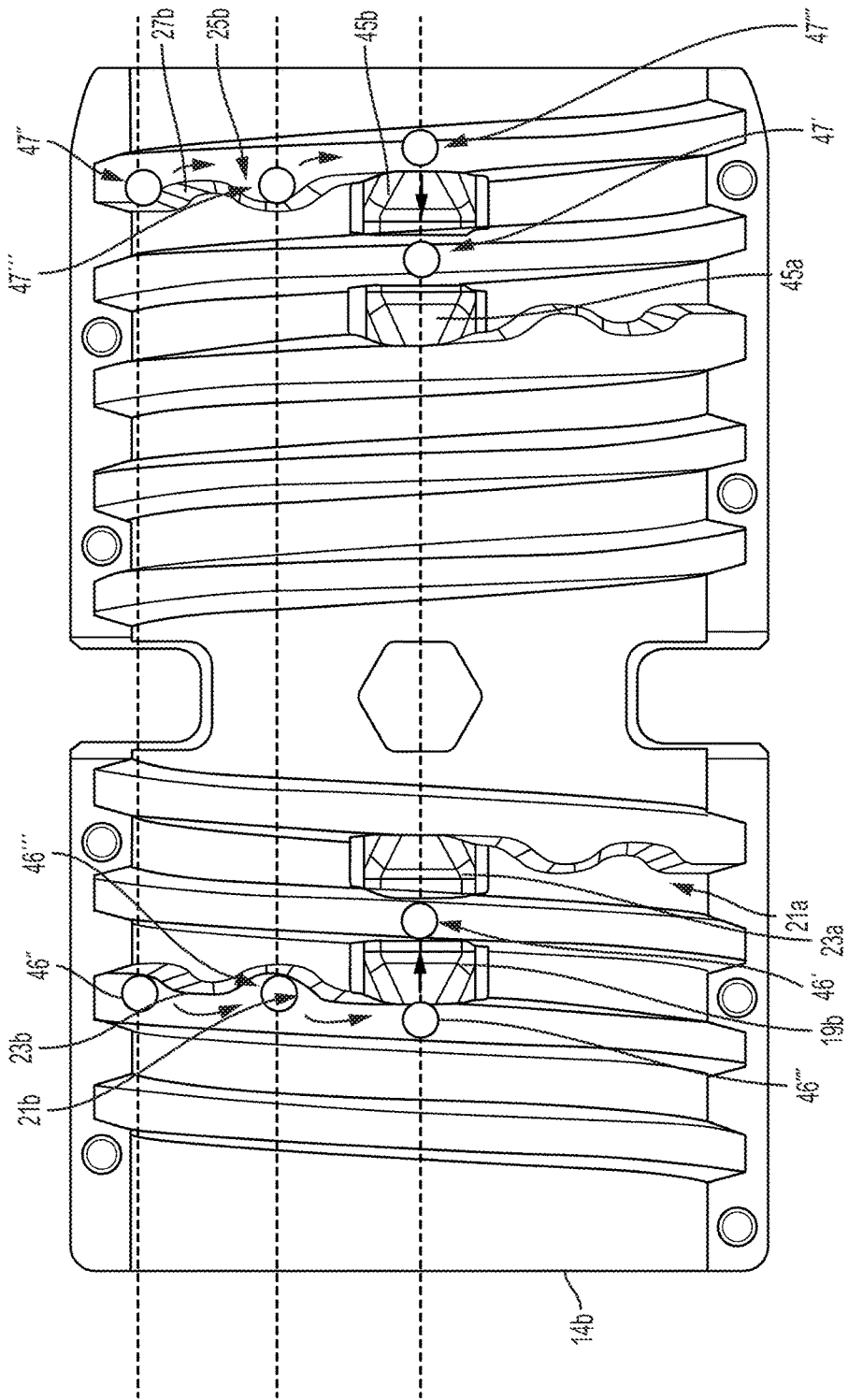
FIG. 26 is a side cross-sectional view of a portion of the actuator of FIG. 10 showing movement of pins.

FIG. 26 illustrates another embodiment of the actuation of the second actuator 14 and the movement of the first and second drums 44*a*, 44*b*, the first pin(s) 46 coupled to the first drum 44*a*, and the second pin(s) 47 coupled to the second drum 44*b* in response thereto, thereby causing movement of the first and second actuation shafts and, hence, causing angular movement of the end effector 8. In this illustrated embodiment, locations of first and second pins 46', 47' in the first and second threads 42*a*, 42*b*, respectively, correspond to the first position of the second actuator 14 in which the end effector 8 is in its unarticulated position. A location of pin 46" corresponds to the position of the pin 46' after the second actuator 18 has been almost rotated 350° from its first position to its fourth position, with the pin 46" not yet having moved over the ramp 23*b*. Similarly, a location of pin 47" corresponds to the position of the pin 47' after the second actuator 18 has been almost rotated 350° from its first position to its fourth position, with the pin 47" not yet having moved over the ramp 27*b*. A location of pin 46''' corresponds to the position of the pin 46" after the second actuator 18 has been rotated 350° from its first position to its fourth position, with the pin 46''' being positioned in the detent 21*b* adjacent to the ramp 23*b* it just traversed over. Similarly, a location of pin 47''' corresponds to the position of the pin 47" after the second actuator 18 has been rotated 350° from its first position to its fourth position, with the pin 47''' being positioned in the detent 25*b* adjacent to the ramp 27*b* it just traversed over. A location of pin 46'''' corresponds to the position of the pin 46''' after the second actuator 18 has been rotated 360° from its first position to its fifth position, at which point the pin 46'''' is free to slide proximally through the longitudinal cut-out 19*b* back to its initial position (location of the pin 46'). Similarly, a location of pin 47'''' corresponds to the position of the pin 47''' after the second actuator 18 has been rotated 360° from its first position to its fifth position, at which point the pin 47'''' is free to slide distally through the longitudinal cut-out 45*b* back to its initial position (location of the pin 47').

FIGS. 27-30 illustrate another embodiment of a surgical device 100. The device 100 can generally be configured and used similar to the surgical device 2 of the embodiment of FIG. 1 and similar to other embodiments of surgical devices described herein. The device 100 can include a proximal handle portion 102 including a main housing 118, a shaft assembly 104 extending distally from the handle portion 102, an end effector (not shown) including a pair of opposed jaws (or, in other embodiments, another type of working element) and being coupled to a distal end of the shaft assembly 104 at a pivot joint (not shown), spacers (not shown), electrodes (not shown), a first actuator 106 configured to effect the opening and closing of the opposed jaws and including a latch 106*a*, a second actuator 108 configured to effect articulation of the end effector, a third actuator 110 configured to rotate the shaft assembly 104 and the end effector about a longitudinal axis A1 of the shaft assembly 104, a fourth actuator 112 configured to translate a cutting element (not shown) along the end effector, a fifth actuator 114 configured to turn on and off the application of energy, a sixth actuator 122 configured to cause return of the end effector from an articulated position to an unarticulated position, an actuation mechanism operatively connected to the second actuator 108 and operatively connected to the sixth actuator 122, a stationary handle 116 including a latch 116*a*, stabilizing members each including a pair of washers 124 and a clip 126, a bend region (not shown), and a bias spring 128 configured to bias the closure trigger 106 open.

The device 100 in this illustrated embodiment includes an electrical connection 120 configured to couple to a conductive lead (not shown), such as an RF cable, etc., and can hence be powered. In other embodiments, the surgical device can be unpowered, e.g., not be configured to apply energy to tissue.

The second actuator 108 of the device 100 can be configured to effect articulation of the end effector similar to the second actuator 14 of the device 2 discussed above, but the second actuator 108 in this illustrated embodiment has a different configuration than the second actuator 14 of the device 2 discussed above. The second actuator 108 in this illustrated embodiment can generally be configured and used similar to second actuators of surgical devices having articulatable end effectors described in previously mentioned U.S. patent application Ser. No. 14/658,944 entitled "Methods and Devices for Actuating Surgical Instruments" filed on Mar. 16, 2015.

The actuation mechanism operatively connected to the second actuator 108 can have a variety of sizes, shapes, and configurations. As in this illustrated embodiment, the actuation mechanism can be coupled to the proximal handle portion 102 of the device 100 and can include the second actuator 108, which as described herein can be configured to be manually actuated by a user to effect articulation of the end effector. As in this illustrated embodiment, as shown in FIGS. 27-32, the second actuator 108 can include a ring-shaped portion configured to be accessible to a user outside the main housing 118 and can include an elongate tubular portion extending proximally from the ring-shaped portion and being configured to be contained within the main housing 118. The second actuator 108 can thus be cannulated.

The second actuator 108 can include first and second threads 130*a*, 130*b* formed in an internal surface 108*i* thereof. The first thread 130*a* can be associated with the first actuation shaft 131*a* (see FIG. 32) of the device 100, and the second thread 130*b* can be associated with the second actuation shaft 131*b* (see FIG. 32) of the device 100, as discussed further below. The first and second threads 130*a*, 130*b* can be independent from one another, as in this illustrated embodiment, with each of the first and second threads 130*a*, 130*b* defining separate paths. The first and second threads 130*a*, 130*b* can wind in opposite directions around the second actuator 108, e.g., one left-handed and one right-handed. The first and second threads 130*a*, 130*b* can have any length around the second actuator's internal surface 130*i*. In an exemplary embodiment, the first and second threads 130*a*, 130*b* can have the same length around the second actuator's internal surface 108*i*, which can facilitate symmetrical articulation of the end effector. The first and second threads 130*a*, 130*b* in this illustrated embodiment includes grooves configured to mate with corresponding protrusions configured to slide within the grooves. In other embodiments, the first and second threads 130*a*, 130*b* of the second actuator 108 can include protrusions configured to slidably mate with corresponding grooves.

The actuation mechanism can include first and second drums 132a, 132b, which are shown in FIGS. 29-33, configured to movably mate with the second actuator 108. The second drum 132b is also shown as a standalone element in FIG. 34. The first and second drums 132a, 132b can have a variety of sizes, shapes, and configurations. The first nut 132a can be associated with the first actuation shaft 131a, and the second nut 132b can be associated with the second actuation shaft 131b, as discussed further below. As in this illustrated embodiment, each of the first and second drums 132a, 132b can be generally cylindrical in shape and can be cannulated. The first and second drums 132a, 132b can each be configured to be disposed within the cannulated interior of the second actuator 108, as illustrated in FIGS. 29-32.

The first drum 132a can be biased distally, and the second drum 132b can be biased proximally. The first and second drums 132a, 132b can thus be biased to opposite directions. The device 100 can include one or more biasing elements 134 configured to bias the first drum 132a proximally and the second drum 132b distally. The one or more biasing elements 134 in this illustrated embodiment includes a plurality of springs that balance one another to urge the first drum 132a in the proximal direction and to urge the second drum 132b in the distal direction. The bias force provided to the first and second drums 132a, 132b by the one or more biasing elements 134 can be overcome during actuation of the second actuator 108 to move the first and second drums 132a, 132b from their biased positions, as discussed further below. As also discussed further below, the one or more biasing elements 134 can be configured to facilitate auto return of the end effector to its unarticulated position.

Figure 35:
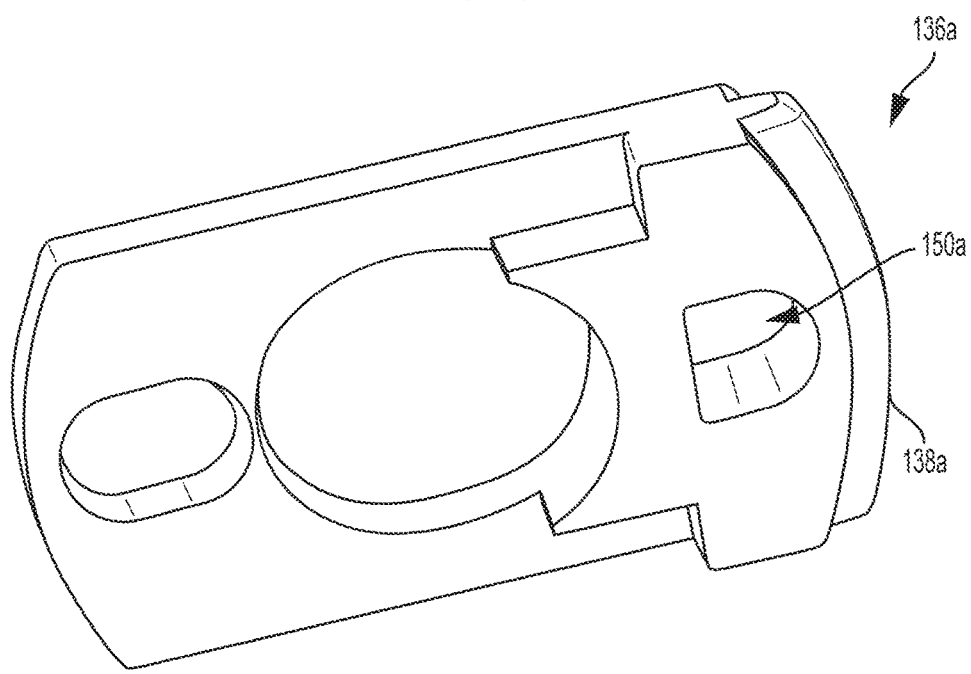
FIG. 35 is a perspective view of a thread block of the device of FIG. 27.

As shown in FIGS. 29-33, the first drum 132a can have first and second thread blocks 136a, 136b coupled thereto, and the second drum 132b can have third and fourth thread blocks 136c, 136d coupled thereto. The first thread block 136a is also shown as a standalone element in FIG. 35. Each of the thread blocks 136a, 136b, 136c, 136d can include a protrusion 138a, 138b, 138c, 138d extending therefrom. The thread blocks 136a, 136b, 136c, 136d each include a single protrusion 138a, 138b, 138c, 138d in this illustrate embodiment, but in other embodiments, any one or more of the thread blocks can include more than one protrusion extending therefrom. The first and second thread blocks 136a, 136b (e.g., the first and second protrusions 138a, 138b thereof) associated with the first drum 132a can be configured to slidably move within the first thread 130a of the second actuator 108, and the third and fourth thread blocks 136c, 136d (e.g., the third and fourth protrusions 138c, 138d thereof) associated with the second drum 132b can be configured to slidably move within the second thread 130b of the second actuator 108. In other embodiments in which the first and second threads 130a, 130b of the second actuator 108 include protrusions configured to slidably mate with corresponding grooves, the thread blocks coupled to each of the drums 132a, 132b can include grooves configured to engage the protrusions.

In response to actuation of the second actuator 108, e.g., in response to a user's rotation of the second actuator 108, the second actuator 108 can be configured to rotate about a longitudinal axis A3 (shown in FIG. 28) thereof. As in this illustrated embodiment, the second actuator's longitudinal axis A3 can be coaxial with the shaft assembly's longitudinal axis A1. The second actuator 108 can be configured to remain stationary along its longitudinal axis A3 during the rotation. In other words, the second actuator 108 can be configured to not move distally or proximally during its rotation. The rotation of the second actuator 108 can cause the first and second drums 132a, 132b disposed within the second actuator 108 and threadably engaged therewith via the thread blocks 136a, 136b, 136c, 136d (e.g., the first thread 130a threadably engaged with the first and second thread blocks 136a 136b via the first and second protrusions 138a, 138b thereof, and the second thread 130b threadably engaged with the third and fourth thread blocks 136c, 136d via the third and fourth protrusions 138c, 138d thereof) to simultaneously move. The opposed threading of the first and second threads 130a, 130b can cause the first and second drums 132a, 132b to move in opposite directions. One of the first and second drums 132a, 132b can move proximally, and the other of the first and second drums 132a, 132b can move distally. The movement of the first and second drums 132a, 132b can include longitudinal translation along the second actuator's longitudinal axis A3, which as in this illustrated embodiment, can also be along the shaft assembly's longitudinal axis A1. The first and second drums 132a, 132b can be configured to alternately move distally and proximally during the actuation of the second actuator 108. In other words, rotation of the second actuator 108 in a same direction, whether it be clockwise or counterclockwise, can cause the first drum 132a to first move distally and the second drum 132b to move proximally, and then cause the first and second drums 132a, 132b to switch directions so that the first drum 132a moves proximally and the second drum 132b moves distally. The first actuator shaft 131a can be operatively connected to the first drum 132a, as discussed herein, such that the movement of the first drum 132a can cause a force to be applied to the first actuator shaft 131a and thereby cause corresponding movement of the first actuator shaft 131a, e.g., longitudinal translation of the first drum 132a in a proximal direction can cause longitudinal translation of the first actuator shaft 131a in the proximal direction. The second actuator shaft 131b can be operatively connected to the second drum 132b, as discussed herein, such that the movement of the second drum 132b can cause a force to be applied to the second actuator shaft 131b and thereby cause corresponding movement of the second actuator shaft 131b, e.g., longitudinal translation of the second drum 132b in a distal direction can cause longitudinal translation of the second actuator shaft 131b in the distal direction. The movement of the first and second actuator shafts 131a, 131b can be configured to cause the end effector to articulate.

The first actuator shaft 131a can be operatively connected to the first drum 132a and the second actuator shaft 131b can be operatively connected to the second drum 132b in a variety of ways. For example, as mentioned above, and as shown in FIGS. 30 and 32, first and second stabilizing members can be seated within their respective associated drums 132a, 132b.

The first and second stabilizing members can be configured to facilitate actuation of the second actuator 108, and hence facilitate articulation of the end effector, regardless of the rotational position of the shaft assembly 104 about the shaft assembly's longitudinal axis A1. In other words, the third actuator 110 can be configured to be at any rotational position about the longitudinal axis A1 when the second actuator 108 is actuated to articulate the end effector. The rotation of the shaft assembly 6 can rotate the first and second actuation shafts 131a, 132b of the shaft assembly 104, as discussed herein, which adjusts the position of the first and second actuation shafts 131a, 131b relative to the second actuator 108 and to the actuation mechanism. The first and second stabilizing members can be configured to rotate within and relative to their respective drums 132a, 132b during rotation of the shaft assembly 104 in response to actuation of the third actuator 110. Accordingly, regardless of the rotational position of the first and second stabilizing members relative to their respective drums 132a, 132b, the first and second actuation shafts 131a, 131b coupled to the first and second stabilizing members can be moved proximally/distally in response to the proximal/distal movement of the drums 132a, 132b during actuation of the second actuator 108. Similar to the first and second stabilizing members, the third stabilizing member can be configured to facilitate actuation of the fourth actuator 112, and hence facilitate movement of the cutting element, regardless of the rotational position of the shaft assembly 104 about the shaft assembly's longitudinal axis A1.

Each of the first drum's associated thread blocks 136a, 136b can be configured to be alternately seated in and withdrawn from the first thread 130a. The first drum's associated thread blocks 136a, 136b can thus be configured to retractable, e.g., move radially inward. Each of the first drum's associated thread blocks 136a, 136b can be biased into being seated in the first thread 130a, e.g., biased radially outward. The biasing can be provided by a bias element 140a, 140b, which includes two springs in this illustrated embodiment that each engage both of the thread blocks 136a, 136b. When a bias force applied to the thread blocks 136a, 136b by their associated bias elements 140a, 140b is overcome, e.g., by actuation of the sixth actuator 122, the thread blocks 136a, 136b can retract from the first thread 130a. Similarly, each of the second drum's associated thread blocks 136c, 136d can be configured to be alternately seated in and withdrawn from the second thread 130b. The second drum's associated thread blocks 136c, 136d can thus be configured to retractable. Each of the second drum's associated thread blocks 136c, 136d can be biased into being seated in the second thread 130b. The biasing can be provided by a bias element 140c, 140d, which includes two springs in this illustrated embodiment that each engage both of the thread blocks 136c, 136d. When a bias force applied to the thread blocks 136c, 136d by their associated bias elements 140c, 140d is overcome, e.g., by actuation of the sixth actuator 122, the thread blocks 136c, 136d can retract from the second thread 130b. As discussed further below, the retraction of the thread blocks 136a, 136b from the first thread 130a and the retraction of the thread blocks 136c, 136d from the second thread 130b can cause the end effector to auto return to its unarticulated position from an articulated position.

Figure 27:
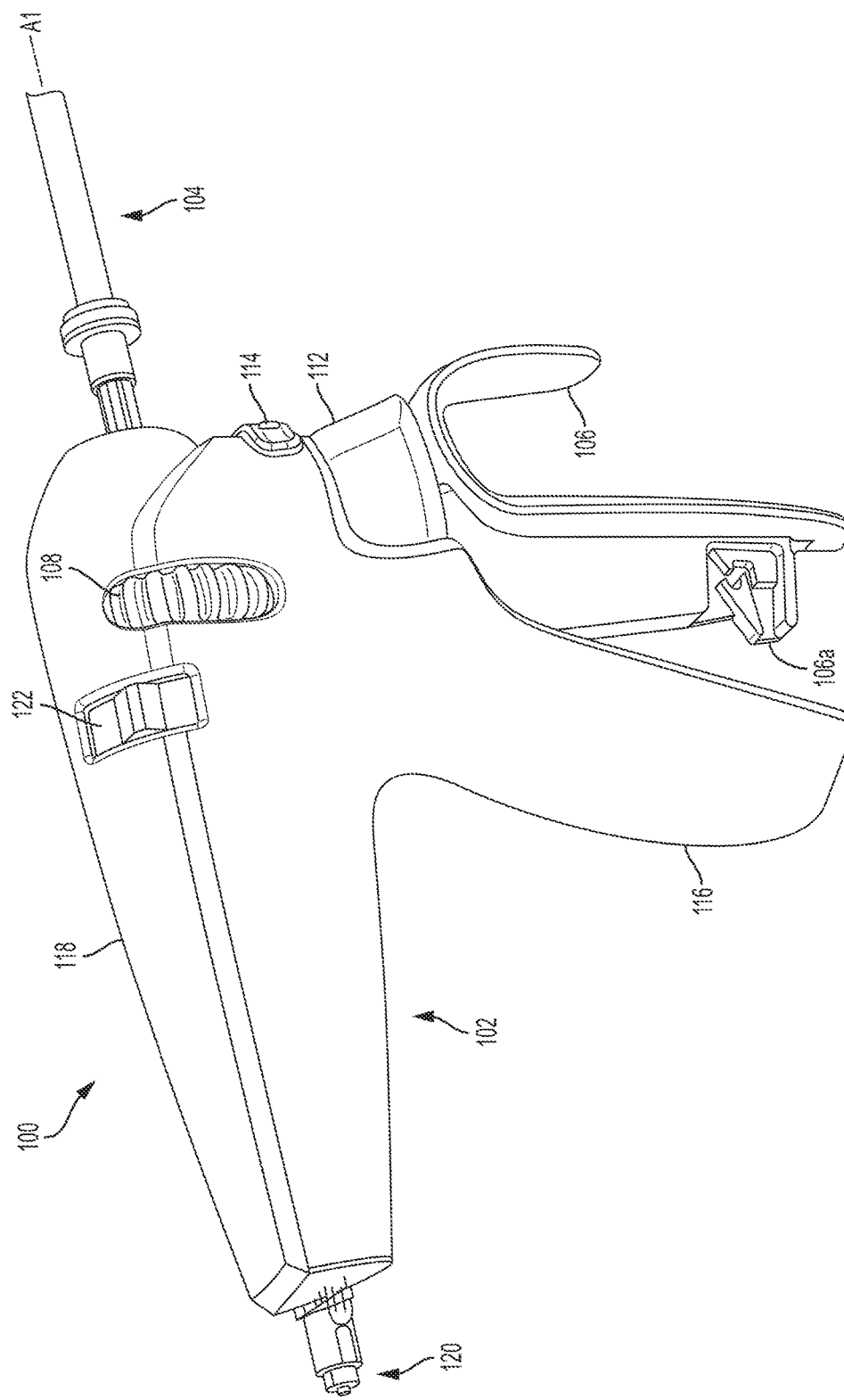
FIG. 27 is a partial perspective view of another embodiment of a surgical device with select elements of the device omitted for clarity of illustration.
Figure 28:
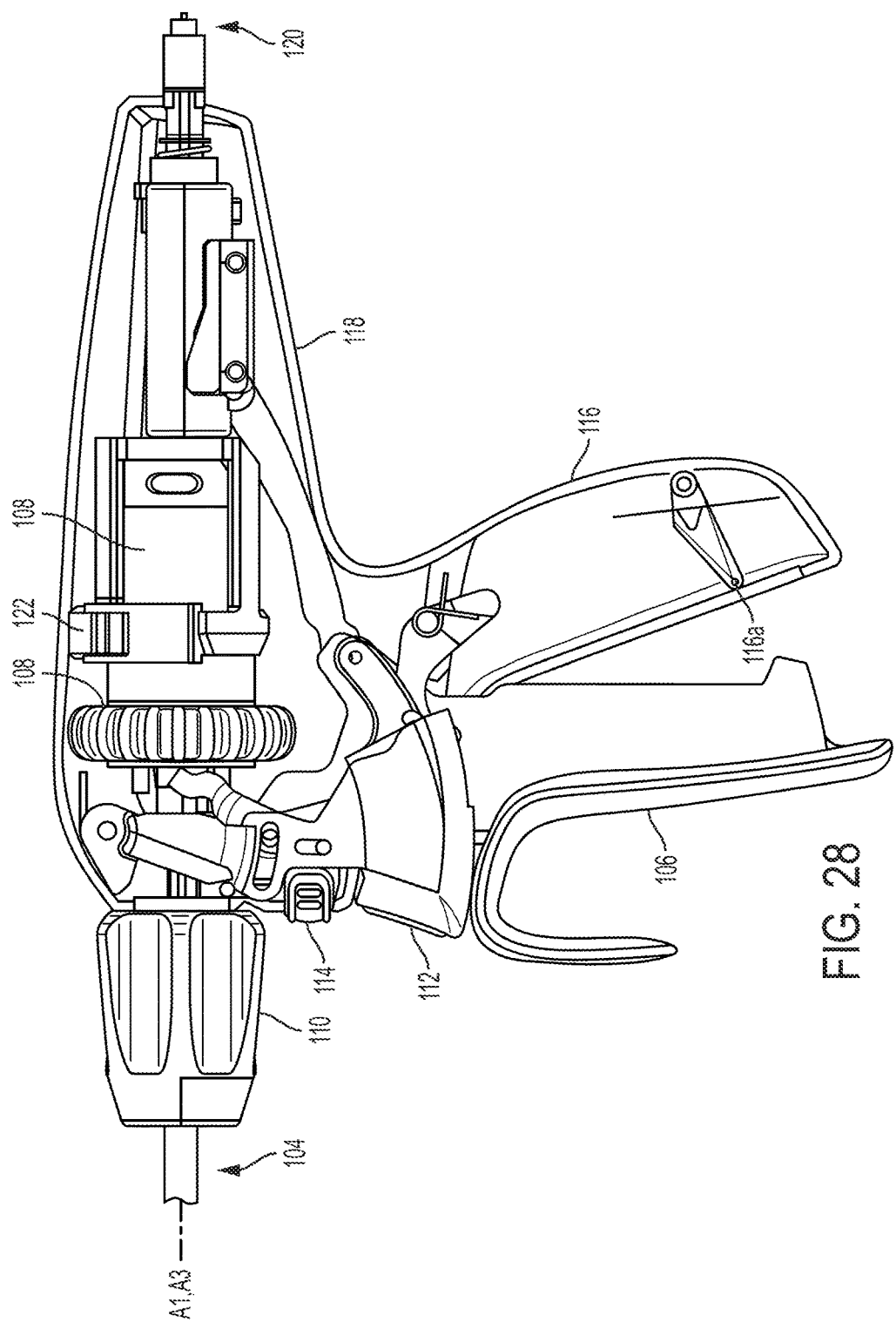
FIG. 28 is a side cross-sectional view of a proximal portion of the device of FIG. 27.
Figure 29:
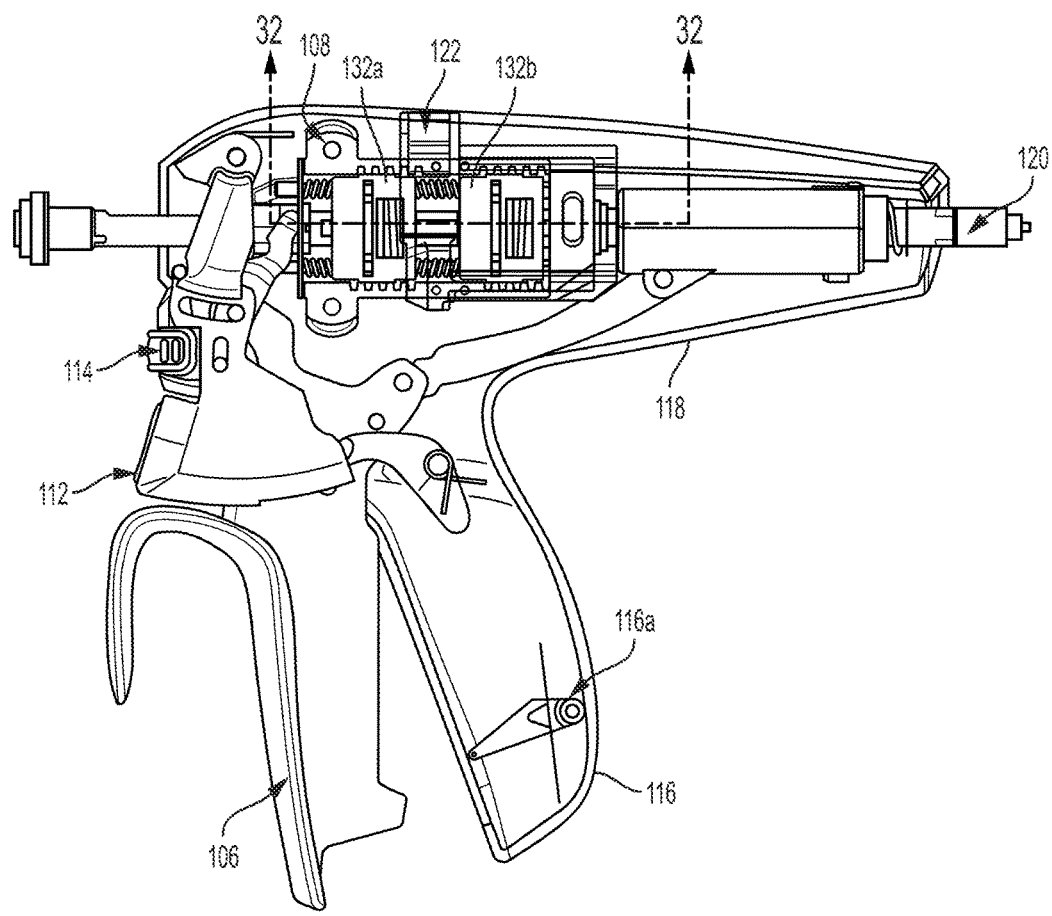
FIG. 29 is a side partially cross-sectional view of a proximal portion of the device of FIG. 27 with select elements of the device omitted for clarity of illustration.
Figure 30:
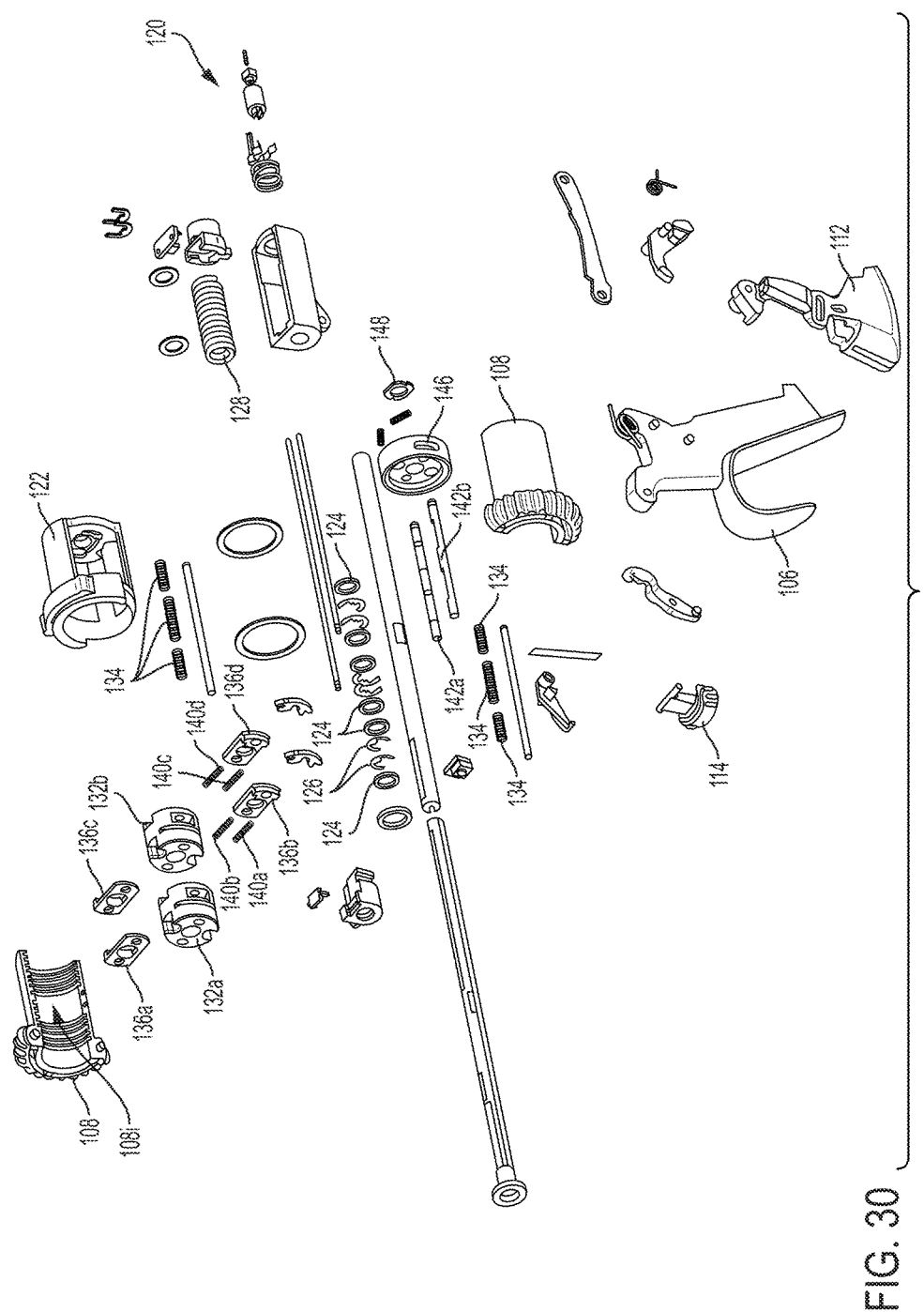
FIG. 30 is a exploded view of a proximal portion of the device of FIG. 27 with select elements of the device omitted for clarity of illustration.
Figure 31:
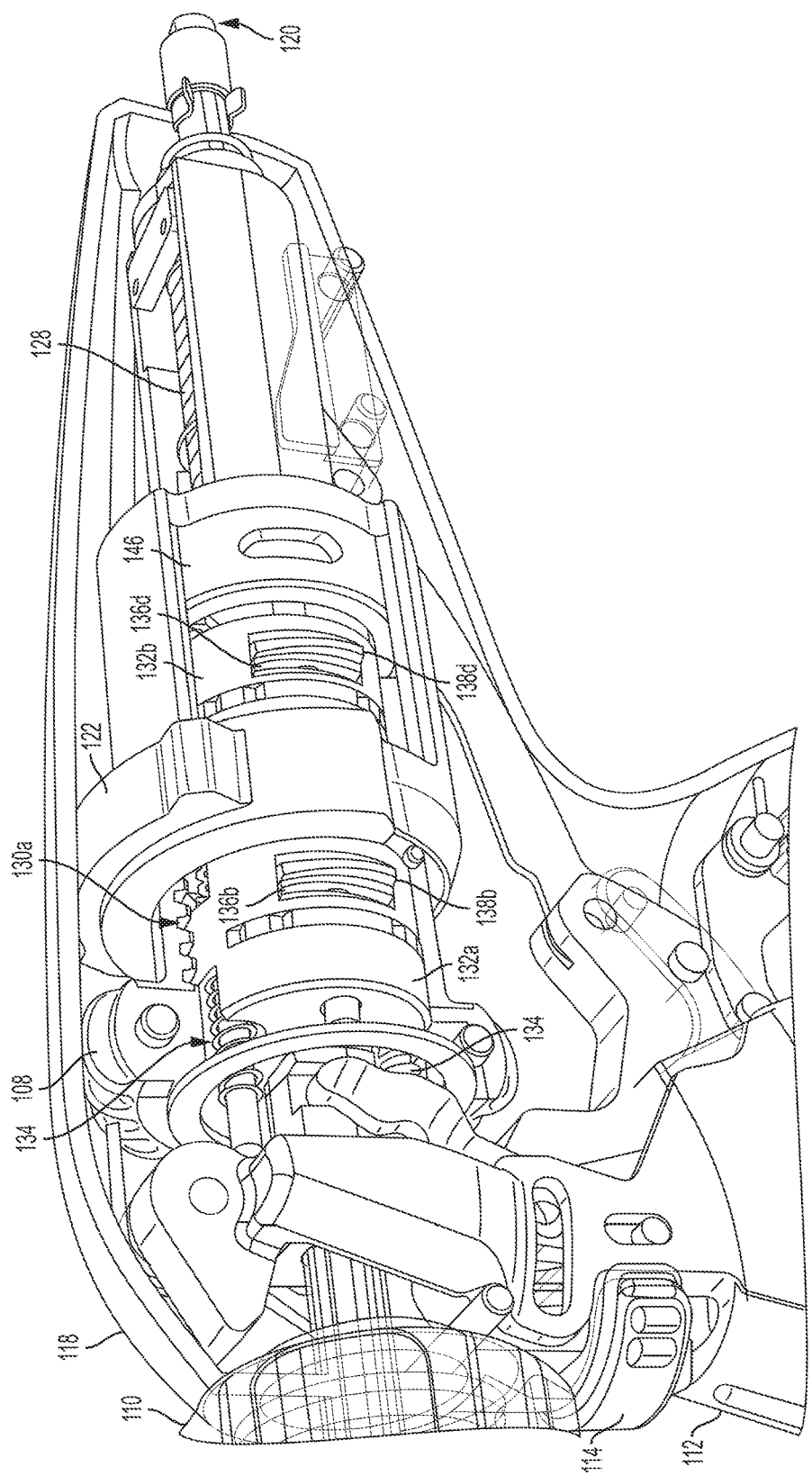
FIG. 31 is a perspective partially cross-sectional view of a proximal portion of the device of FIG. 27.
Figure 36:
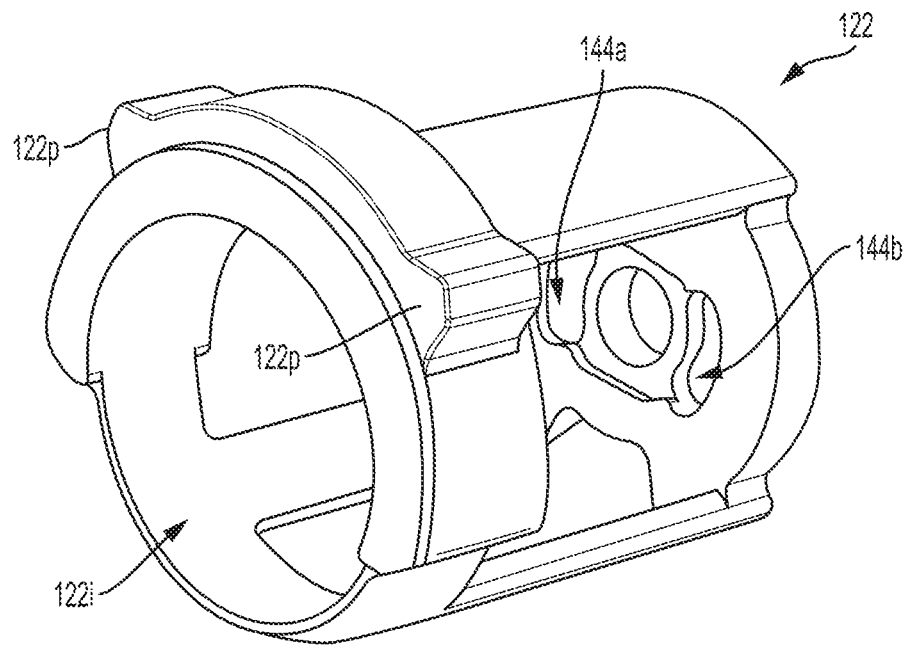
FIG. 36 is a perspective view of an actuator of the device of FIG. 27.

Unlike the device 2 discussed above, the device 100 in the illustrated embodiment of FIG. 27 includes the sixth actuator 122 configured to be actuated to cause end effector auto return. The sixth actuator 122 is shown as a standalone element in FIG. 36. In general, the sixth actuator 122 can be configured to be accessible outside of the device's main housing 118. In an exemplary embodiment, the sixth actuator 122 can be configured to be manually accessed and manipulated from both sides (left and right) of the device 100, which may facilitate manipulation of the sixth actuator 122 regardless of whether the user manipulating the sixth actuator 122 is left handed or right handed.

The sixth actuator 122 can have a variety of sizes, shapes, and configurations. As in this illustrated embodiment, the sixth actuator 122 can include a switch configured to be selectively moved to effect auto return of the end effector. Movement of the sixth actuator 122 in one direction (e.g., clockwise) can be configured to cause articulation of the end effector in one direction (e.g., right) and rotation of the sixth actuator 122 in the opposite direction (e.g., counterclockwise) can be configured to cause articulation of the end effector in the second direction (e.g., left). The sixth actuator 122 can, as in this illustrated embodiment, include a cylindrical toggle ring with an inner lumen 122i extending therethrough so as to be cannulated to allow extension of various elements of the device 100 therethrough, as shown in FIGS. 28, 29, 31, and 32. The sixth actuator 122 can include protrusions 122p thereon configured to be accessible from outside the device's main housing 118. The protrusions 122p can be configured to be manually pushed with a finger, surgical tool, or other element to urge the sixth actuator 122 either clockwise or counterclockwise, depending on a direction of the manually pushing. The second actuator 122 can be rigid.

Figure 32:
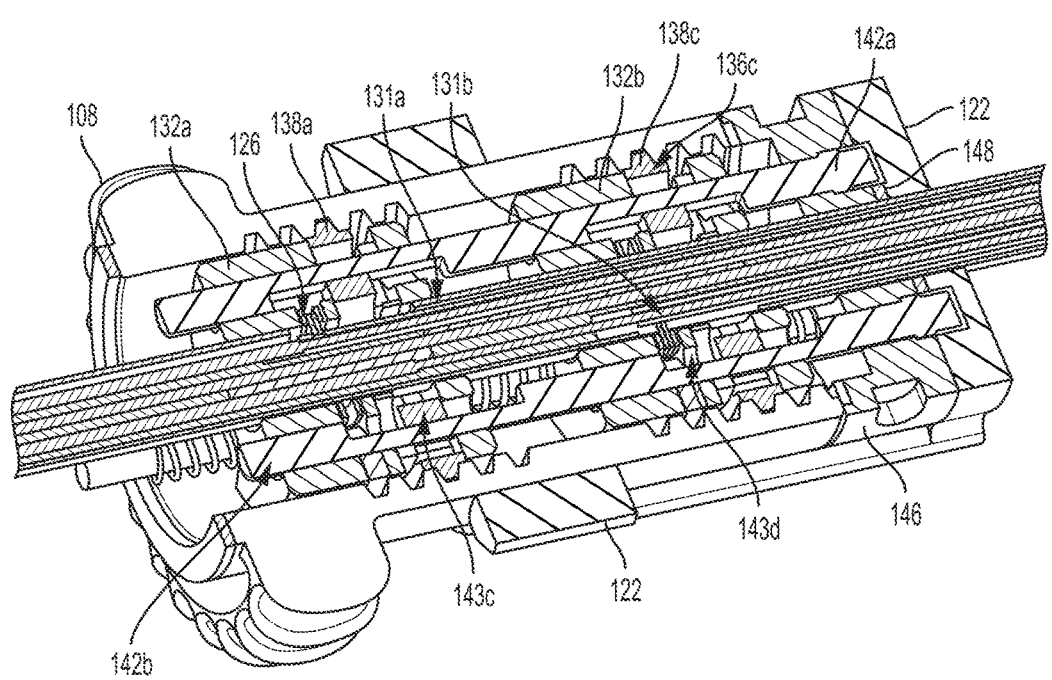
FIG. 32 is a perspective cross-sectional view of a portion of the device of FIG. 27 within a handle thereof.
Figure 37:
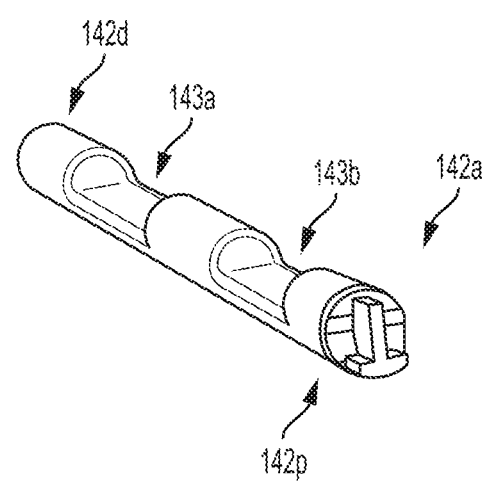
FIG. 37 is a perspective view of a reset bar of the device of FIG. 27.

The device 100 can include a pair of reset bars 142a, 142b (see FIGS. 30 and 32) operatively coupled to the sixth actuator 122. The first and second reset bars 142a, 142b can have a variety of sizes, shapes, and configurations. As in this illustrated embodiment, the reset bars 142a, 142b can include elongate members, as shown in FIG. 32. FIG. 37 shows the first bar 142a as a standalone element. The first reset bar 142a can have proximal and distal ends 142p, 142d. The first reset bar 142a can include first and second cut-outs 143a, 143b formed therein. As shown, the first reset bar 142a can have a half-moon or semi-circular cross-sectional shape at the cut-outs 143a, 143b and can have one or more other cross sectional shapes at the other portions thereof between the proximal and distal ends 142p, 142d. In this illustrated embodiment, the other cross-sectional shape(s) along the first reset bar's longitudinal length include a circular cross-sectional shape therealong except in a proximal portion where the first reset bar 142a has a T-shaped cross-sectional shape. As in this illustrated embodiment, the second reset bar 142b can be the same as the first reset bar 142a and similarly include proximal and distal ends and third and fourth cut-outs 143c, 143d (see FIG. 32).

The proximal end of each of the reset bars 142a, 142b can be configured to seat in first and second cavities 144a, 144b, respectively, formed in an interior surface of the sixth actuator 122. The reset bars 142a, 142b can be configured to move (e.g., rotate) within their respective cavities 144a, 144b in response to actuation of the sixth actuator 122 to facilitate end effector auto return, as discussed further below. The cavities 144a, 144b can thus each have a size and shape that allows movements of their respective reset bars 142a, 142b therein.

Figure 33:
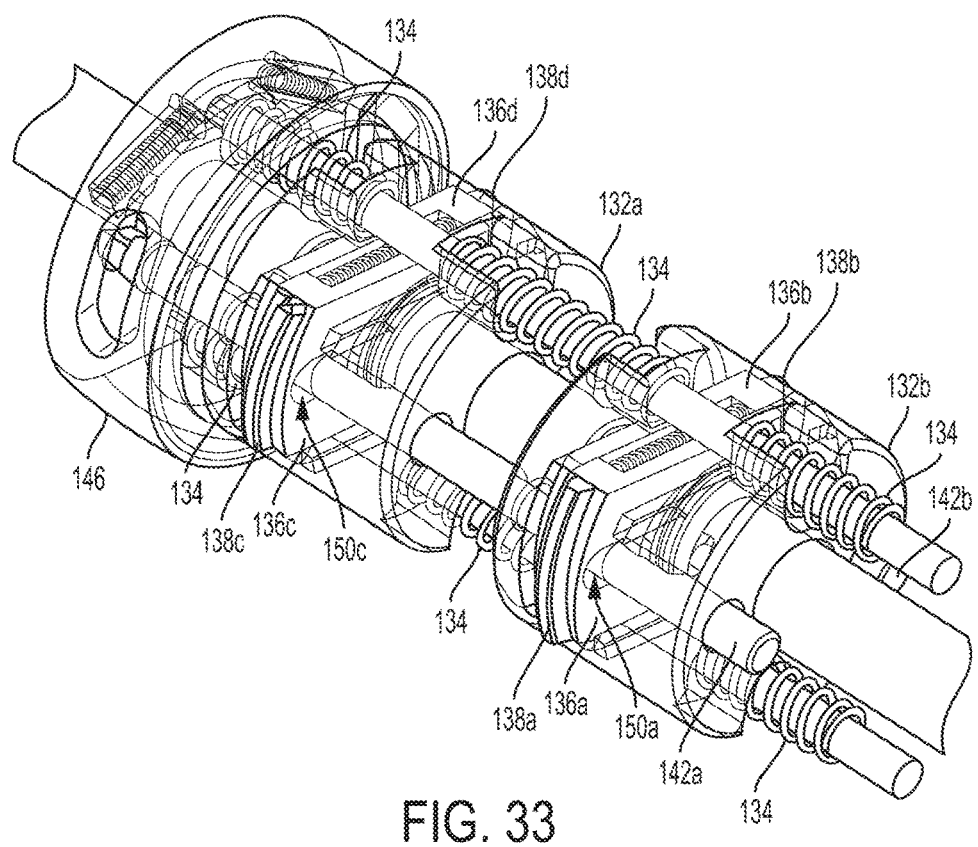
FIG. 33 is a perspective partially transparent view of a portion of the device of FIG. 27 within a handle thereof.
Figure 34:
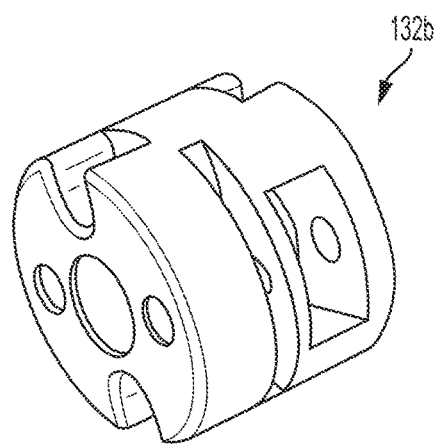
FIG. 34 is a perspective view of a drum of the device of FIG. 27.
Figure 34A:
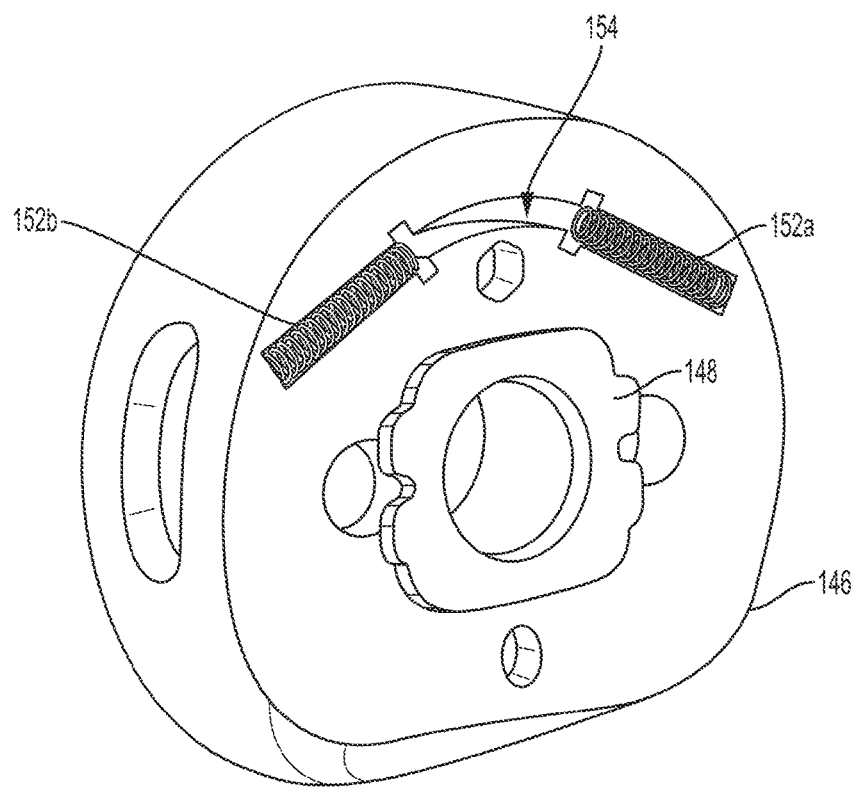
FIG. 34A is a perspective view of a support member, a cam, and bias elements of the device of FIG. 27.

As also shown in FIGS. 32 and 33, the reset bars 142a, 142b can extend distally from the cavities 144a, 144b through a cam 148, through a support member 146 (also shown in FIG. 34A), through the second drum 130b and through holes 150c, 150d in the third and fourth thread blocks 136c, 136d coupled thereto, through the first drum 130a and through holes 150a, 150b in the first and second thread blocks 136a, 136b coupled thereto, and the second actuator 108. The proximal cut-outs 143b, 143d of the first and second reset bars 142a, 142b can be positioned within the holes 150c, 150d of the third and fourth thread blocks 136c, 136d, and the distal cut-outs 143a, 143c of the first and second reset bars 142a, 142b can be positioned within the holes 150a, 150b of the first and second thread blocks 136a, 136b. The reset bars 142a, 142b can each have a longitudinal length that allows the reset bars 142a, 142b to be fully contained within the second and sixth actuators 108, 122, as shown in FIG. 32, which may help prevent the movement of the reset bars 142a, 142b from interfering with any unintended elements of the device 100.

The reset bars 142a, 142b can each be operatively coupled to the cam 148 (see FIGS. 30, 32, and 38) positioned between a proximal surface of the support member 146 and the interior surface of the sixth actuator 122 that has the cavities 144a, 144b formed therein. As discussed further below, the cam 148 can be configured to move and cause corresponding movement of the reset bars 142a, 142b within the cavities 144a, 144b in response to actuation of the sixth actuator 122.

The support member 146 can be configured to be biased to a central, default position. The support member 146 is shown in the central, default position in FIGS. 31-33. The support member 146 can be biased to the central, default position in a variety of ways, such as with a pair of bias elements 152a, 152b, which include springs in this illustrated embodiment, seated in a cavity 154 formed in the proximal surface of the support member 146. As discussed further below, the actuation of the sixth actuator 122 (e.g., the pushing thereof in either a clockwise or counterclockwise direction) can be configured to counteract the bias force provided by one of the bias elements 152a, 152b, with the one of the bias forces being counteracted depending on which direction the sixth actuator 122 is moved, and thereby allow the support member 146 to be moved to an offset position from the central, default position.

Figure 38:
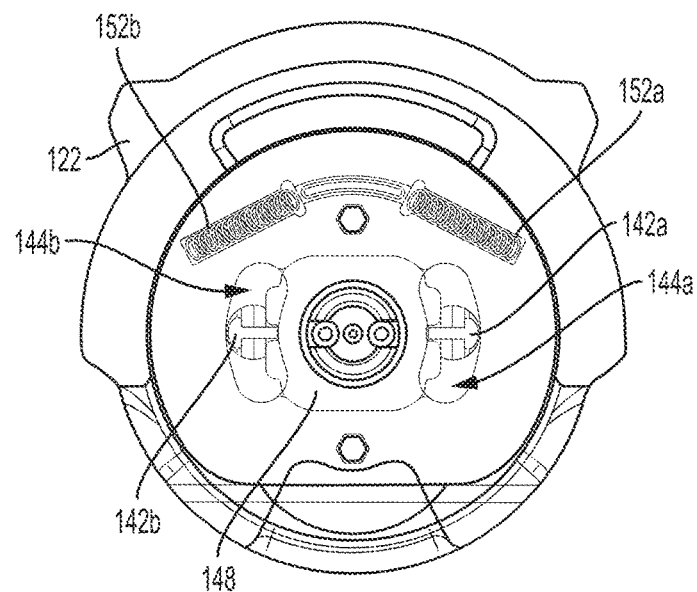
FIG. 38 is a partially transparent, cross-sectional end view of the device of FIG. 27 with the actuator of FIG. 36 in a first position.
Figure 39:
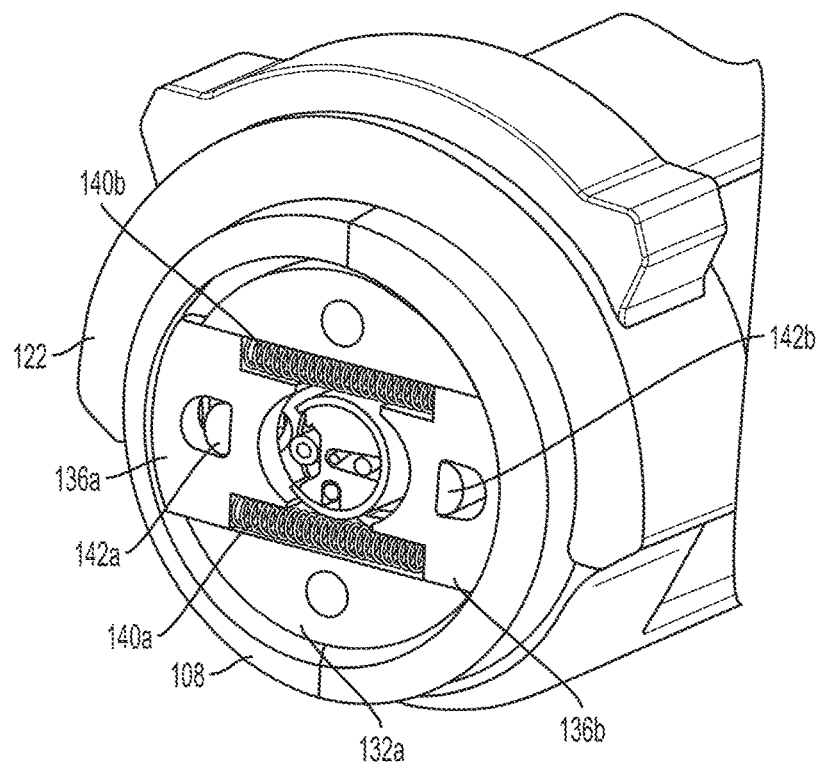
FIG. 39 is a perspective view of the device of FIG. 38.

FIGS. 38-41 illustrate an embodiment of the actuation of the sixth actuator 122 and the movement of the first and second reset bars 142a, 142b in response thereto, thereby causing movement of the first and second actuation shafts 131a, 131b and, hence, causing angular movement of the end effector. FIGS. 38 and 39 illustrate a first, default position of the sixth actuator 122 in which the support member 146 is in its central, default position, the bias elements 140a, 140b are biasing the protrusions 138a, 138b of the first and second thread blocks 136a, 136b into threaded engagement with the first thread 142a, and the bias elements 140c, 140d are biasing the protrusions 138c, 138d of the third and fourth thread blocks 136c, 136d into threaded engagement with the second thread 142b. The planar side of the reset bars' cut-outs 143a, 143b, 143c, 143d can face radially inward, as shown in FIG. 39 (the proximal cut-outs 143b, 143d are obscured in FIG. 39). When the sixth actuator 122 is in first, default position, any one or more of the first, second, third, fourth, and fifth actuators 106, 108, 110, 112, 114 can be actuated any number of times to cause their various effects.

Figure 40:
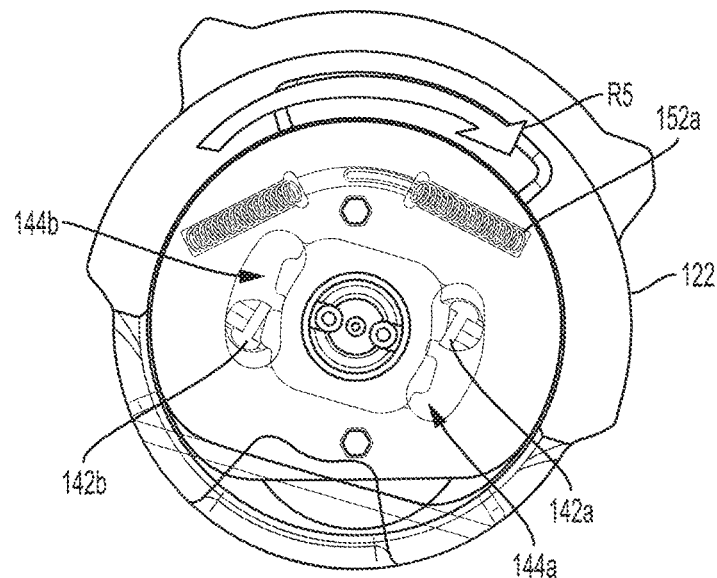
FIG. 40 is a partially transparent, cross-sectional end view of the device of FIG. 38 with the actuator in a second position.
Figure 41:
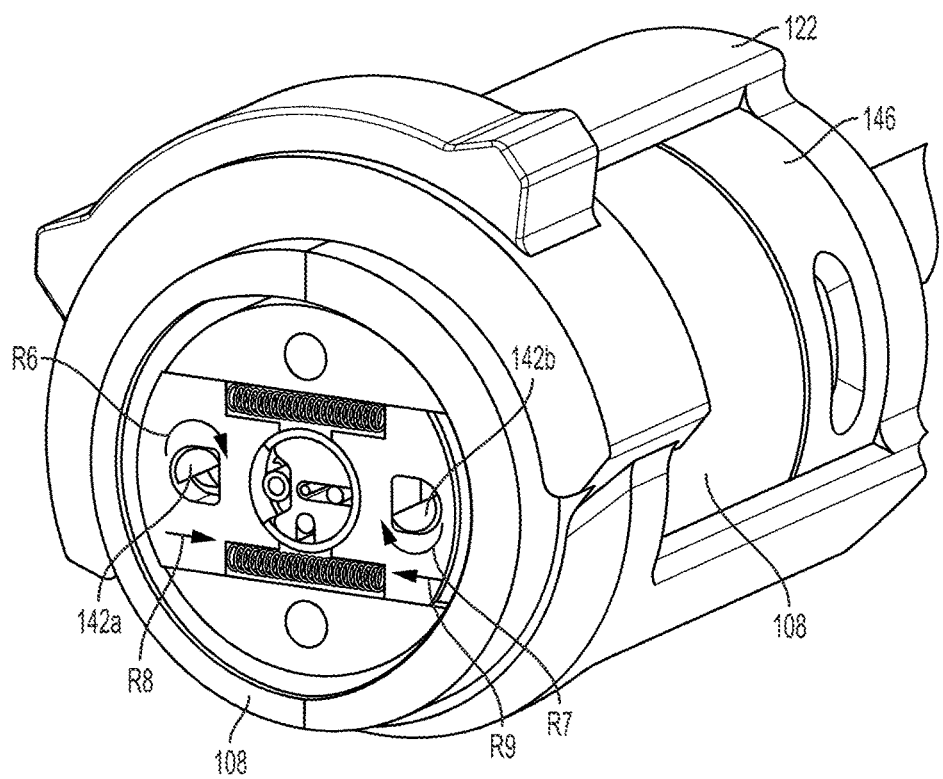
FIG. 41 is a perspective view of the device of FIG. 40.

FIGS. 40 and 41 illustrate a second, actuated position of the sixth actuator 122 in which the sixth actuator 122 has been moved from the first, default position of FIGS. 38 and 39. The sixth actuator 122 has been moved clockwise in this illustrated embodiment, as indicated by arrow R5 in FIG. 40. The movement of the sixth actuator 122 can be relative to the second actuator 108 such that the sixth actuator 122 rotates around the second actuator 108. The movement of the sixth actuator 122 can cause the first and second reset bars 142a, 142b to rotate and to slide within the cavities 144a, 144b of the sixth actuator 122, as shown in FIG. 40, and to rotate within the holes 150a, 150b, 150c, 150d of the thread blocks 136a, 136b, 136c, 136d. The movement (e.g., rotation and sliding) of the first and second reset bars 142a, 142b can cause the cam 148 to rotate, as shown in FIG. 40. The rotation of the sixth actuator 122 can cause the first and second reset bars 142a, 142b to rotate in opposite directions from one another, as shown by arrows R6, R7 in FIG. 41. The rotation of the first and second reset bars 142a, 142b in the holes 150a, 150b, 150c, 150d of the thread blocks 136a, 136b, 136c, 136d can cause the planar side of the reset bars' cut-outs 143a, 143b, 143c, 143d to no longer face radially inward, as shown in FIG. 41 (the proximal cut-outs 143b, 143d are obscured in FIG. 41). The reset bars 142a, 142b thus begin to exert a force on the thread blocks 136a, 136b, 136c, 136d that counteracts the bias force provided by the bias elements 140a, 140b, 140c, 140d that bias the thread blocks 136a, 136b, 136c, 136d radially outward. The thread blocks 136a, 136b, 136c, 136d are thus urged radially inward by the movement of the reset bars 142a, 142b, as shown by arrows R8, R9 in FIG. 41, thereby causing the protrusions 138a, 138b, 138c, 138d to become disengaged from the first and second threads 130a, 130b. In other words, the thread blocks 136a, 136b, 136c, 136d retract radially inward so as to no longer be threadably engaged with the second actuator 108. With the second actuator 108 no longer being threadably engaged by the thread blocks 136a, 136b, 136c, 136d, the first and second drums 132a, 132b are free to longitudinally translate within the second actuator 108 to their default positions therein (the first drum 132a moving proximally and the second drum 132b moving distally), as urged by the biasing elements 134. Accordingly, the first and second actuation shafts 131a, 131b operatively coupled to the first and second drums 132a, 132b, respectively, can be caused to move proximally (first actuation shaft 131a) or distally (second actuation shaft 131b). The first and second shafts 131a, 131b will thus no longer be causing articulation of the end effector such that the end effector can return to its unarticulated position.

Release of the sixth actuator 122 from its second, actuated position can cause the sixth actuator 122 to automatically return to its first, default position due to the bias elements 152a, 152b seated in the support member 146 that is operatively coupled to the sixth actuator 122.

The sixth actuator 122 can be configured to be actuated to cause end effector auto return when the end effector is articulated at any non-zero angle relative to the shaft assembly's longitudinal axis A1. Readjustment of the end effector's angular position may thus be effected quickly during performance of a surgical procedure.

Although the sixth actuator 122 has been moved clockwise in the illustrated embodiment of FIGS. 38-41 to cause end effector auto return, the sixth actuator 122 can instead be moved counterclockwise to cause end effector auto return, as discussed herein. The counterclockwise movement of the sixth actuator 122 can cause end effector auto return similar to that discussed above for the clockwise movement of the sixth actuator 122 with various elements (e.g., the cam 148, the reset bars 142a, 142b, etc.) instead moving in opposite directions than their directions of movement in response to clockwise movement of the sixth actuator 122.

FIGS. 42-45 illustrate another embodiment of the actuation of the sixth actuator 122 and the movement of the first and second reset bars 142a, 142b in response thereto, thereby causing movement of the first and second actuation shafts 131a, 131b and, hence, causing angular movement of the end effector. In this illustrated embodiment, the second actuator 108 is actuated to rotate the shaft assembly 104 and the end effector prior to the actuation of the sixth actuator 122.

Figure 42:
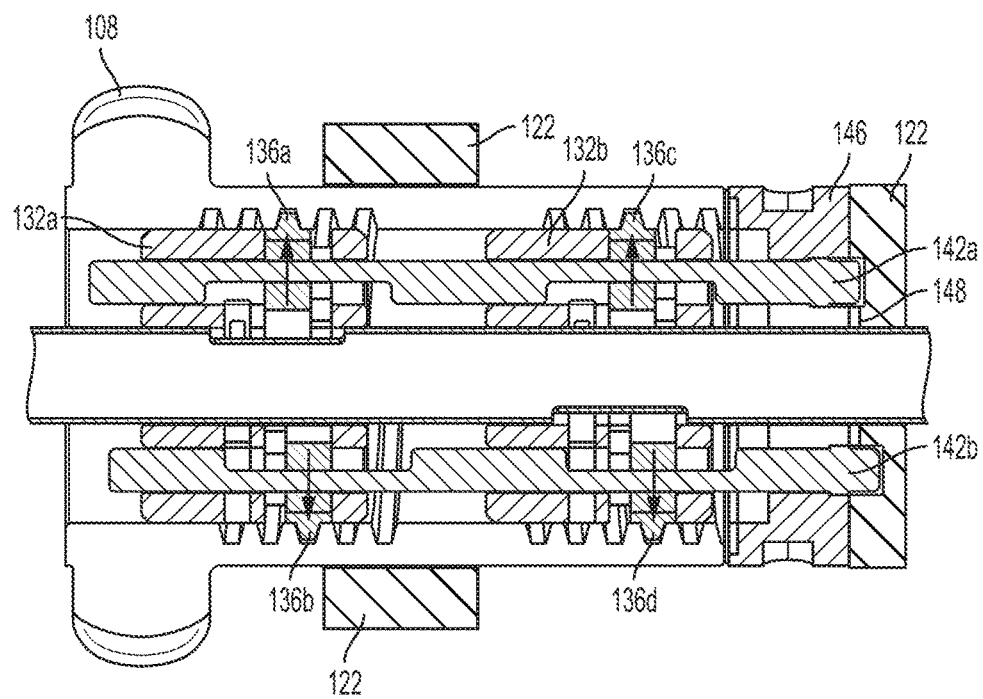
FIG. 42 is a side cross-sectional view of a portion of the device of FIG. 27 within a handle thereof with the actuator of FIG. 36 in a first position and a second actuator in a first position.

FIG. 42 illustrate the second actuator 108 in a first position in which the thread blocks 136a, 136b, 136b, 136d are threadably engaged with the first and second threads 130a, 130b, respectively. With the first position of the second actuator 108, similar to the embodiment of FIG. 18 in which the second actuator 14 is in the first position, the end effector of the device 100 is at its unarticulated position and the first and second actuation shafts 131*a*, 131*b* have substantially aligned proximal ends. The sixth actuator 122 is in its first, default position in FIG. 42.

Figure 43:
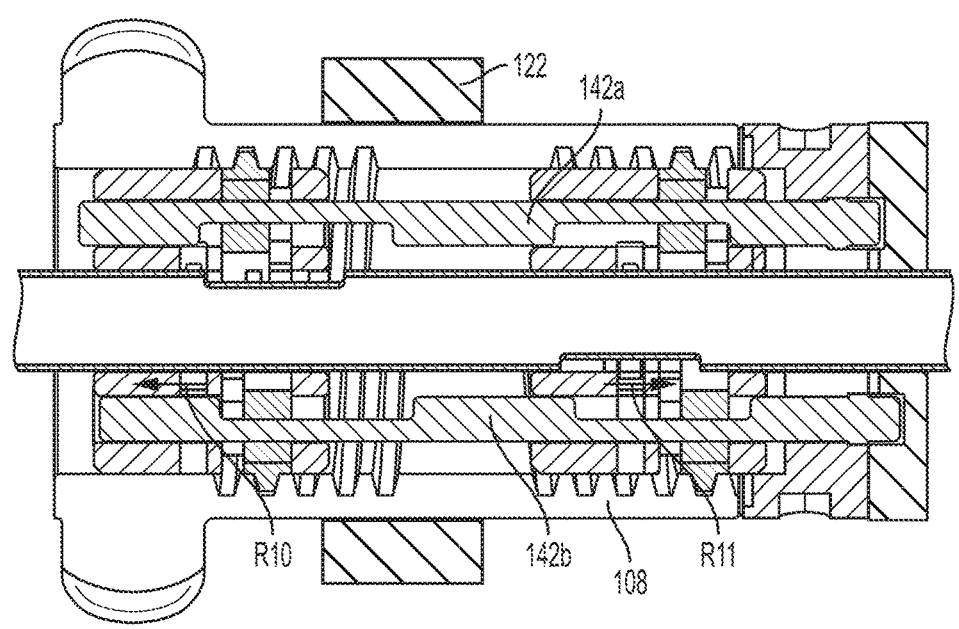
FIG. 43 is a side cross-sectional view of a portion of the device of FIG. 42 with the second actuator in a second position.

FIG. 43 illustrates a second position of the second actuator 108 in which the second actuator 108 has been rotated from the first position of FIG. 42, e.g., rotated clockwise, to fully articulate the end effector, e.g., articulate the end effector to its maximum extent in one direction. The rotation of the second actuator 108 has caused the first drum 132*a* to move distally, as shown by arrow R10 pointing distally, and the second drum 132*b* to move proximally, as shown by arrow R11 pointing proximally. The first drum 132*a* has moved within the second actuator 108 due to the threaded engagement of the first and second thread blocks 136*a*, 136*b* coupled to the first drum 132*a* with the second actuator's first thread 130*a*, and the second drum 132*b* has moved within the second actuator 108 due to the threaded engagement of the third and fourth thread blocks 136*c*, 136*d* coupled to the second drum 132*b* with the second actuator's second thread 130*b*. The rotation of the second actuator 108 has caused the first and second drums 132*a*, 132*b* to move farther apart so as to be separated from each other by greater distance than in FIG. 42. The distal movement of the first drum 132*a* has caused the first actuation shaft 131*a* operatively connected thereto to correspondingly move distally. Similarly, the proximal movement of the second drum 132*b* has caused the second actuation shaft 131*b* operatively connected thereto to correspondingly move proximally. The end effector has accordingly articulated to the one side, e.g., left, from its position in FIG. 42. The sixth actuator 122 has not moved in response to the actuation of the second actuator 108 between FIGS. 42 and 43, e.g., has remained in its first position. Also, the RF cable, the third actuation shaft, and the fourth actuation shaft have not moved in response to the actuation of the second actuator 108 between FIGS. 42 and 43.

Figure 44:
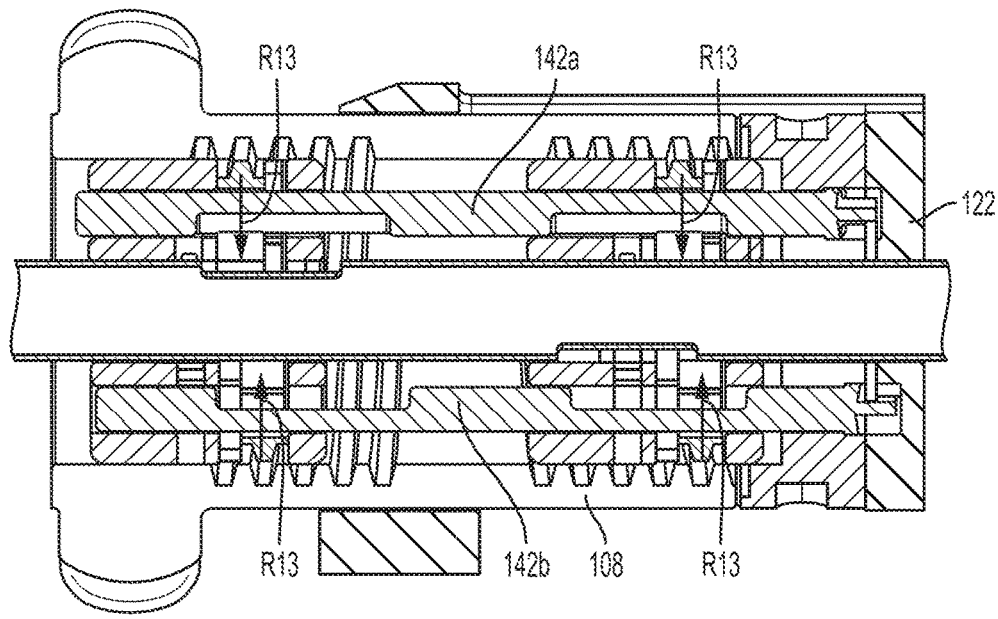
FIG. 44 is a side cross-sectional view of a portion of the device of FIG. 43 with the actuator in a second position.
Figure 45:
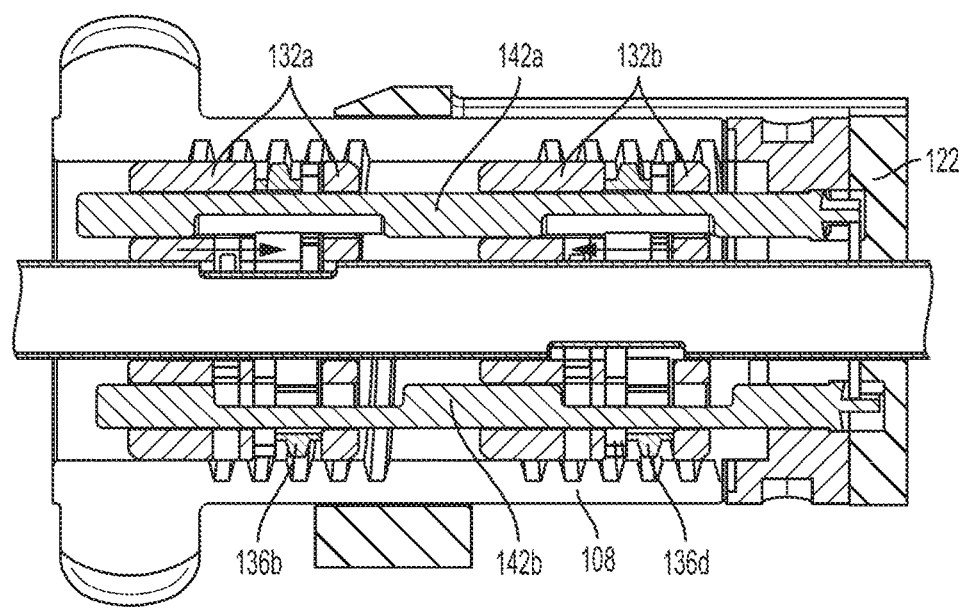
FIG. 45 is a side cross-sectional view of a portion of the device of FIG. 44 with the actuator in the second position.

FIG. 44 illustrates the sixth actuator 122 in its second, actuated position to which the sixth actuator 122 has been moved from the first, default position of FIGS. 42 and 43 due to actuation of the sixth actuator 122, e.g., rotation of the sixth actuator 122. The actuation of the sixth actuator 122 has caused the first and second reset bars 142*a*, 142*b* to rotate from their position in FIGS. 42 and 43, thereby exerting a force on the thread blocks 136*a*, 136*b*, 136*c*, 136*d*, with the first reset bar 132*a* exerting a force on the first and third thread blocks 136*a*, 136*c* and the second reset bar 132*b* exerting a force on the second and fourth thread blocks 136*b*, 136*d*. The force exerted on the thread blocks 136*a*, 136*b*, 136*c*, 136*d* causes the thread blocks 136*a*, 136*b*, 136*c*, 136*d* to move radially inward from their position in FIGS. 42 and 43, as shown by arrows R13 in FIG. 44, and thereby become disengaged from the first thread 130*a* (first and second thread blocks 136*a*, 136*b*) and the second thread 130*b* (third and fourth thread blocks 136*c*, 136*d*). Accordingly, as shown in FIG. 45, the first and second drums 132*a*, 132*b* are free to longitudinally translate within the second actuator 108 to their default positions therein (the first drum 132*a* moving proximally and the second drum 132*b* moving distally). Also, as urged by the biasing elements 134, and the first and second actuation shafts 131*a*, 131*b* operatively coupled to the first and second drums 132*a*, 132*b*, respectively, can be caused to move proximally (first actuation shaft 131*a*) or distally (second actuation shaft 131*b*). The first and second shafts 131*a*, 131*b* will thus no longer be causing articulation of the end effector such that the end effector can return to its unarticulated position.

Release of the sixth actuator 122 from its second, actuated position of FIGS. 44 and 45 can cause the sixth actuator 122 to automatically return to its first, default position of FIGS. 42 and 43 due to the bias elements 152*a*, 152*b* seated in the support member 146 that is operatively coupled to the sixth actuator 122.

The sixth actuator 122 has been rotated clockwise in this illustrated embodiment to cause end effector auto return, but as mentioned above, the sixth actuator 122 can instead be rotated counterclockwise to similarly cause end effector auto return.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
 an elongate shaft having a longitudinal axis;
 an end effector at a distal end of the elongate shaft, the end effector being movable between a first position aligned along the longitudinal axis and a second position angularly oriented relative to the longitudinal axis; and
 a handle coupled to a proximal end of the elongate shaft, the handle comprising
   a first actuator having a first mode in which movement of the end effector between the first and second positions is controlled by rotation of the first actuator, and the first actuator having a second mode in which the first actuator is operatively disengaged from the end effector such that the end effector can move from the second position to the first position, and
   a second actuator configured to be rotated so as to cause the first actuator to move from the first mode to the second mode and thereby move the end effector from the second position to the first position.

2. The device of claim 1, wherein the first actuator is configured to automatically return to the first mode from the second mode.

3. The device of claim 1, further comprising an electrical connection configured to couple to a conductive lead.

4. The device of claim 1, wherein the first actuator is configured to be manually actuated to cause the end effector to move from the first position to the second position.

5. The device of claim 1, wherein the second actuator includes a switch that is configured to be selectively moved to cause the end effector to automatically return to the first position from the second position.

6. A surgical device, comprising:
 a handle having an elongate shaft extending distally therefrom with an end effector at a distal end of the elongate shaft, the end effector having first and second jaws configured to engage tissue therebetween;
 first and second elongate members extending through the elongate shaft; and
 an actuation assembly having
   first and second movable members operatively coupled to the end effector such that axial translation of the first and second movable members causes the end effector to move between a first orientation, in which the end effector is axially aligned with the elongate shaft, and a second orientation, in which the end effector is angularly oriented relative to the elongate shaft, and an actuator engaged with the first and second movable members such that rotation of the actuator is effective to cause axial translation of the first and second movable members; and wherein the first movable member includes a first drum coupled to the first elongate member, and the second movable member includes a second drum coupled to the second elongate member;

wherein, when the end effector is in the second orientation, the first and second movable members can selectively freely axially translate relative to the actuator to cause the end effector to move from the second orientation to the first orientation; and wherein the actuation of the actuator is configured to simultaneously move the first drum in a first direction and cause axial translation of the first elongate member and move the second drum in a second direction and cause axial translation of the second elongate member, the axial translations of the first and second elongate members causing the end effector to move from the first orientation to the second orientation, and the second direction being opposite to the first direction.

7. The device of claim 6, further comprising a second actuator coupled to the handle;

wherein actuation of the second actuator is configured to disengage the first and second movable members from the actuator and thereby cause the end effector to move from the second orientation to the first orientation.

8. The device of claim 7, wherein the first and second movable members are each threadably engaged with the actuator when the end effector is in the second orientation until the actuation of the second actuator.

9. The device of claim 7, wherein the second actuator is configured to be actuated with the end effector at any angular orientation relative to the elongate shaft.

10. The device of claim 7, wherein the second actuator includes a switch that is configured to be selectively moved to cause the end effector to automatically return to the first orientation from the second orientation.

11. The device of claim 6, wherein the first and second movable members are configured to be disengaged from the actuator with the end effector at any angular orientation relative to the elongate shaft.

12. The device of claim 6, wherein the actuation of the actuator includes rotation of the actuator, the first and second movable members being configured to automatically axially translate when the actuator is rotated beyond a predetermined threshold amount of rotation.

13. The device of claim 12, wherein the first and second movable members are each threadably engaged with the actuator until the actuator is rotated beyond the predetermined threshold amount of rotation.

14. The device of claim 6, wherein the first and second movable members are configured to be disengaged from the actuator only once the end effector has reached a maximum amount of angular movement relative to the elongate shaft.

15. The device of claim 6, wherein the actuation of the actuator includes rotation of the actuator, and the actuator is configured to require more force to rotate when the end effector is in the second orientation than when the end effector is in the first orientation.

16. The device of claim 6, wherein the first and second members are configured to become temporarily threadably disengaged from the actuator while the end effector is moving from the second orientation to the first orientation.

17. The device of claim 6, wherein the engagement of the first and second movable members with the actuator includes a threaded engagement.

18. The device of claim 6, further comprising an electrical connection configured to couple to a conductive lead.

19. The device of claim 6, wherein the actuator is configured to be manually actuated to cause the end effector to move from the first orientation to the second orientation.

20. A surgical device, comprising:

an elongate shaft extending distally from a handle, an end effector being at a distal end of the elongate shaft, and the end effector having first and second jaws configured to engage tissue therebetween; and an actuation assembly comprising
first and second movable members operatively coupled to the end effector such that axial translation of the first and second movable members causes the end effector to move between a first orientation, in which the end effector is axially aligned with the elongate shaft, and a second orientation, in which the end effector is angularly oriented relative to the elongate shaft, and an actuator configured to be rotated and thereby cause the axial translation of the first movable member in a first direction and the axial translation of the second movable member in a second direction that is opposite the first direction, and a second actuator, wherein actuation of the second actuator is configured to disengage the first and second movable members from the first actuator and thereby cause the end effector to move from the second orientation to the first orientation.

* * * * *